United States Patent
Hohman et al.

(10) Patent No.: US 10,875,828 B2
(45) Date of Patent: Dec. 29, 2020

(54) MITHRENE AND METHODS OF FABRICATION OF MITHRENE

(71) Applicant: THE REGENTS OF THE UNIVERSITY OF CALIFORNIA, Oakland, CA (US)

(72) Inventors: James Nathan Hohman, Menlo Park, CA (US); Mary S. Collins, Oakland, CA (US); Tess E. Smidt, Berkeley, CA (US)

(73) Assignee: The Regents of the University of California, Oakland, CA (US)

(*) Notice: Subject to any disclaimer, the term of this patent is extended or adjusted under 35 U.S.C. 154(b) by 85 days.

(21) Appl. No.: 16/322,830

(22) PCT Filed: Aug. 4, 2017

(86) PCT No.: PCT/US2017/045609
§ 371 (c)(1),
(2) Date: Feb. 1, 2019

(87) PCT Pub. No.: WO2018/038898
PCT Pub. Date: Mar. 1, 2018

(65) Prior Publication Data
US 2019/0194128 A1    Jun. 27, 2019

Related U.S. Application Data

(60) Provisional application No. 62/371,700, filed on Aug. 5, 2016.

(51) Int. Cl.
| | |
|---|---|
| *C07C 391/02* | (2006.01) |
| *H01L 51/00* | (2006.01) |
| *C07C 395/00* | (2006.01) |
| *B01J 31/02* | (2006.01) |
| *B01J 35/00* | (2006.01) |
| *C23C 16/06* | (2006.01) |
| *H01L 51/05* | (2006.01) |
| *H01L 51/42* | (2006.01) |
| *H01L 51/50* | (2006.01) |

(52) U.S. Cl.
CPC ......... *C07C 391/02* (2013.01); *B01J 31/0272* (2013.01); *B01J 35/004* (2013.01); *C07C 395/00* (2013.01); *C23C 16/06* (2013.01); *H01L 51/009* (2013.01); *H01L 51/0091* (2013.01); *H01L 51/0002* (2013.01); *H01L 51/05* (2013.01); *H01L 51/4213* (2013.01); *H01L 51/50* (2013.01)

(58) Field of Classification Search
CPC ............... C07C 391/02; C07C 395/00; H01L 21/02568; H01L 51/00; C23C 16/06
See application file for complete search history.

(56) References Cited

U.S. PATENT DOCUMENTS

| | | | | |
|---|---|---|---|---|
| 4,212,885 A * | 7/1980 | Gitlitz | .................... | A01N 55/04 514/493 |
| 4,965,184 A * | 10/1990 | LeStrange | ................. | G03C 1/10 430/599 |
| 5,554,447 A * | 9/1996 | Bayless, Jr. | .............. | C09K 3/16 428/483 |
| 10,414,668 B1 * | 9/2019 | Vaia | ....................... | C01G 33/00 |
| 2006/0257662 A1 * | 11/2006 | Bujard | .................. | C09C 1/0018 428/404 |
| 2008/0241098 A1 * | 10/2008 | Young | ..................... | A61P 17/06 424/85.2 |
| 2011/0037033 A1 * | 2/2011 | Green | ...................... | B03D 3/00 252/510 |
| 2011/0104876 A1 * | 5/2011 | Allsop | .............. | C23C 16/45595 438/478 |
| 2012/0280209 A1 * | 11/2012 | Bonnell | .................. | H01L 51/42 257/21 |
| 2013/0168255 A1 * | 7/2013 | Frederich | ................. | C25D 7/12 205/123 |
| 2015/0044556 A1 * | 2/2015 | Wang | .................... | H01M 4/139 429/213 |
| 2015/0221930 A1 * | 8/2015 | Manivannan | ........... | C23C 18/50 427/113 |
| 2015/0283482 A1 * | 10/2015 | Hersam | .................... | B03D 3/00 494/37 |
| 2016/0137598 A1 * | 5/2016 | Johnson | ............... | C07D 341/00 544/215 |
| 2016/0263868 A1 * | 9/2016 | Tomoi | .................... | B32B 25/02 |

OTHER PUBLICATIONS

Eichhofer, Andreas, et al., "1-D-Tin(II) Phenylchalcogenolato Complexes 1[Sn(EPh)2](E=S,Se,Te)—Synthesis, Structures, Quantum Chemical Studies and Thermal Behaviour". Eur. J. Inorg. Chem. 2010, pp. 410-418.*

Trang, Brittany, et al., "Tarnishing Silver Metal into Mithrene". J. Am. Chem. Soc. 2018, 140, 13892-13903. DOI: 10.1021/jacs. 8b08878.*

Cuthbert, Heather L., et al., "Synthesis and Structural Characterization of [Cu20Se4(μ3-SePh)12(PPh3)6] and [Ag(SePh)]". Z. Anorg. Allg. Chem. 2002, 628, 2483-2488.*

Schriber, Elyse A., et al., "Mithrene is a Self-Assembling Robustly Blue Luminescent Metal-Organic Chalcogenolate Assembly for 2D Optoelectronic Applications". ACS Appl. Nano Mater. 2018, 1, 7, pp. 3498-3508. Abstract Only.*

(Continued)

*Primary Examiner* — Bret P Chen
(74) *Attorney, Agent, or Firm* — Womble Bond Dickinson (US) LLP

(57) ABSTRACT

Described are metal organochalcognides which are bulk nanomaterials, expressing monolayer properties in their as-synthesized states. Also described are certain novel metal organochalcogenide compositions. Further described are several methods of preparation of metal organochaleogenides, both solution- and vapor deposition-based, and methods of use of the resulting metal chalcogenides in assays and devices.

35 Claims, 27 Drawing Sheets

(56) References Cited

OTHER PUBLICATIONS

Wang, Shenkai, "Submolecular resolution spectroscopic imaging for photoactive molecules and assemblies". Physical Chemistry Student Seminar from the Department of Chemistry and Biochemistry UCLA, 2019, one page. Abstract Only.*

International Search Report and Written Opinion dated Feb. 15, 2018 for International Application No. PCT/US2017/045609 in 13 pages.

Peppe et al., "Coordination Compounds of Indium. Part 42. The Insertion of Indium(I) Halides into Homonuclear Bonds in Non-Aqueous Media", Canadian Journal of Chemistry, NRC Research Press, CA, vol. 62, Jan. 1, 1984, pp. 2798-2802.

Eichhofer et al., "1-D-Tin(II) Phenylchalcogenolato Complexes ∞1[Sn(EPh)2] (E=S, Se, Te)—Synthesis, Structures, Quantum Chemical Studies and Thermal Behaviour", European Journal of Inorganic Chemistry—Chemische Berichte, vol. 2010, No. 3, Jan. 1, 2010, pp. 410-418.

Bochmann et al, "Synthesis, Structure, and Gas-Phase Decomposition of[Cd(EC6H2tBu3)2]2(E?S, Se): First Examples of Low-Coordinate Volatile Cadmium Chalcogenolato Complexes", Angewandte Chemie. International Edition., DE, (Jun. 1, 1990), vol. 29, No. 6, doi:10.1002/anie.199006381, ISSN 0570-0833, pp. 638-639.

Satchell D P N et al, "The Kinetict and Mechanism of the Mercury(II)-ion-promoted Hydrolysis of Diphenyl Disulphide in Aqueous Dioxane Solutions", Journal of Chemical Research—Synopses, Science Reviews Ltd, GB, (Jan. 1, 1988), ISSN 0308-2342, pp. 262-263.

Cuthbert et al, "Synthesis and Structural Characterization of [Cu 20 Se 4 ( 3-SePh) 12 (PPh 3 ) 6 ] and [Ag(SePh)]", Z. Anorg. Allg. Chem., (Jan. 1, 2002), pp. 2483-2488.

Davies et al, "New Copper(I) Derivatives of Organotellurium Com-pounds: Synthesis, Vibrational and '*'Te Miksbauer Spectra", Inorganica Chimica Acta, (Jan. 1, 1978), pp. L217-L220.

Anjali K S et al, "Polylinked adamantanoid structure of Cd(SePh)"2", Inorganic Chemistry Communications, Elsevier, Amsterdam, NL, vol. 3, No. 12, ISSN 1387-7003, (Dec. 1, 2000), pp. 708-710.

Goldani et al, "Silver-Catalyzed Synthesis of Diaryl Selenides by Reaction of Diaryl Diselenides with Aryl Boronic Acids", The Journal of Organic Chemistry, US, (Oct. 18, 2016), vol. 81, No. 22, doi:10.1021/acs.joc.6b02108, ISSN 0022-3263, pp. 11472-11476.

* cited by examiner

MITHRENE AND METHODS OF FABRICATION OF MITHRENE

CROSS-REFERENCE TO RELATED APPLICATIONS

This application is a US National Stage 371 Application of PCT Application No. PCT/US2017/405609 filed on Aug. 4, 2017, which claims priority to U.S. Provisional Patent Application No. 62/371,700, filed Aug. 5, 2016, the entirety of which are hereby incorporated by reference.

STATEMENT REGARDING FEDERALLY SPONSORED RESEARCH OR DEVELOPMENT

This invention was made with government support under Contract No. DE-ACO2-05CH11231 awarded by the U.S. Department of Energy. The government has certain rights in this invention.

FIELD OF THE INVENTION

The present disclosure relates to metal chaicogenides, which express monolayer properties in their as-synthesized states and thus are bulk nanomaterials.

BACKGROUND OF THE INVENTION

A recurring theme in nanoscience is that new properties emerge in materials with reduced dimensionality. For example, the confinement of electronic carriers within isolated layers of 2-dimensional (2D) materials gives rise to new properties. Researchers have studied transition metal diehaleogenides (TMDs) such as $MoS_2$, $MoSe_2$, $WS_2$ and $WSe_2$ for years but these materials have recently resumed in popularity due to the discovery that these TMDs have vastly different properties on the 2D scale, $MoS_2$ and $WS_2$ are inorganic 2D polymers organized, like graphite, in stacks where layers are held together by van der Waals (vdW) forces.

Although layered TMDs are typically indirect band gap semiconductors in their bulk crystalline form, TMD monolayers possess direct band zaps and high charge carrier mobility, a consequence of isolating their constituent 2D semiconductor layers. For instance, transition metal dichalcogenides (e.g. $MoS_2$) undergo an indirect-to-direct bandgap transition when exfoliated to a monocrystalline single-layer. As monolayers, TMDs exhibit useful electronic, optical, mechanical, chemical and thermal properties. These new properties have attracted interest for a variety of device applications, the properties making them suitable for use in devices such as transistors and solar cells. For example, TMDs have high photoconversion efficiency and show promise as semiconductors for solar cells because they have suitable handgaps and extinction coefficients and are cheap, abundant, and robust as well.

Unfortunately, the unique properties of 2D monolayers are lost rapidly with increasing layer number because of strong interlayer coupling. For example, just two layers eradicates TMD photoluminescence. Exploiting monolayers technologically is therefore complicated by the strict requirement for physical isolation. These ultrathin 2D materials are delicate, difficult to create, handle, characterize, and incorporate into devices because of their unique low-dimensional size. Further, the exfoliation methods used to create the flake-like TMD monolayers are insufficient to produce the large-area semiconducting surfaces needed to use TMD-based photovoltaics on a worldwide scale.

Intercalation of molecules between layers has been one strategy for electrically isolating layers in van der Waals solids, but true electrical isolation of 2D layers in a bulk solid has not been reported. Therefore, a metal-organic material could exhibit monolayer emission characteristics without the necessity of exfoliation. Crystalline metal-organic coordination polymers present a distinctive approach to synthesizing low dimensional nanomaterials by exploiting the integration of insulating organic ligands with inorganic phases. The term 'hybrid,' in which a substance is composed of both inorganic and organic constituents, describes a vast catalog of materials, from disordered colloidal composites to porous, crystalline metal-organic frameworks.

The first example of a metal-organic chalcogenide assembly, silver benzeneselenolate, (mithrene, $[AgSePh]_\infty$) was reported by Cuthbert el al., however, only the synthesis was reported; the bulk nanomaterial properties were not recognized, Mithrene is an air-stable, crystalline, hybrid metal-organic coordination polymer and a hybrid crystal, where phase segregation is fully described by the primitive unit cell. The inorganic phase is a 2D polymer composed of silver and selenium. The silver is in a distorted planar hexagonal lattice. The selenium is coordinated above and below each silver hexagon and is attached to the organic phenyl group, projected above and below the 2D lattice. The selenium-bonded phenyl rings coordinate silver metal sites, insulating a continuous 2D silver selenide structure. This material forms readily via dynamic inter-ligand interactions-primarily of non-covalent van derWaals (vdW) character-which drive their self-assembly into crystalline networks. Therefore, the ligands govern the coordination of the metal sites during supramolecular self-assembly. This coordination differs from that of $Ag_2Se$, a hulk inorganic crystal. In contrast, TMDs are layered structures in the bulk, so monolayers maintain the same coordination.

The chemistry of the late transition metal (period VIII-XII) organochalcogenolates offers a rich chemical infra-structure for the design of supramolecular assemblies. Previous methods used to synthesize transition metal chalcogenolate complexes have been accomplished via chalcogenolysis through cleavage of the Se—H bond or the isolation of the reactive selenolate salt (—SeR). These methods are highly successful in isolating a variety of metal-organic products (discrete complexes and coordination polymers), but the use of harsh and odorous reagents and their sensitivity to air and water is not ideal. Historically, coordination polymers are often treated as kinetic side products en route to more elaborate, discrete organometallic clusters. To our benefit, these reactions kinetically favor the formation of coordination polymer over discrete complexes, leading to rapid precipitation of polymer from solution, Notable prior work investigated the structural integrity of several lamellar silver organothiolates which combine discrete organic and inorganic phases in a single unit cell.

By developing new hybrid material systems in which organic spacer layers insulate and decouple the conducting inorganic layers from each other, bulk materials can be created that preserve monolayer semiconducting characteristics. There is a continued need for such novel metal-organic chalcogenide 2D polymers for development of semi-conductor devices. It is believed that bulk semiconductor properties of such materials will readily allow incorporation into practical devices. Further, a need exists for mild, robust and simple preparative methods for metal-organic chalcogenide 2D polymers.

SUMMARY OF INVENTION EMBODIMENTS

Whereas all other nanomaterials have to be reduced in absolute size before new properties emerge, mithrene has been identified herein as an example of a bulk nanomaterial—a bulk material expressing monolayer properties in its as-synthesized state. Several simple, robust and inexpensive methods for the preparation of mithrene and related crystalline metal organic chalcogenide assemblies (MOCHAs) are disclosed herein, along with methods of use in assays and devices.

Accordingly, in one embodiment is provided a method of preparing a crystalline metal chalcogenide of Formula 1: [M-Z-Ar]$_\infty$, the method comprising providing a first solution comprising a metal ion M$^+$, in a first solvent, the metal ion obtained by dissolving a metal component, $M_pX_q$, in the first solvent; providing a second solution comprising a diaryl dichalcogenide, Ar-Z-Z-Ar, in a second solvent; and contacting the first solution with the second solution to provide the metal chalcogenide as a crystalline, hulk nanomaterial. In this method, the metal (M) corresponding to the metal ion (M$^+$) is selected from the group consisting of silver (Ag), lead (Pb), mercury (Hg), gold (Au), copper (Cu), zinc (Zn), tin (Sn), cobalt (Co), thallium (Tl), gallium (Ga), indium (In), and cadmium (Cd), p is 1 or 2. X is selected from the group consisting of O, NO$_3$, SO$_4$, Cl, Br, CH$_3$CO$_2$, CF$_3$, PF$_6$, BF$_4$, and ClO$_4$, q is 1, 2, or 3. Z is sulfur (S), selenium (Se), tellurium (Te), or combinations thereof, and Ar is phenyl or naphthyl.

In another embodiment is provided a vapor phase deposition method for preparing a substrate coated with a film comprising a metal chalcogenide of Formula I: [M-Z-R]$_\infty$. The method comprises providing a substrate comprising a coating of metal, M, or an oxide thereof, and exposing the substrate coated with metal to a vapor phase comprising a first dialkyl or diaryl dichalcogenide, R$_2$Z$_2$, for a time sufficient to provide a film of a first [M-Z-R]$_\infty$ on the substrate. The metal or oxide thereof is selected from the group consisting of silver (Ag), titanium (Ti), zinc (Zn), lead (Pb), copper (Cu), indium (In), gallium (Ga) and cadmium (Cd). Z is sulfur (S), selenium (Se), tellurium (Te),, or combinations thereof. R is phenyl, naphthyl, biphenyl, methyl, ethyl, propyl, butyl or pentyl.

In yet another embodiment is provided a metal-organic chalcogenide composition according to Formula I: [M-Z-R]$_\infty$. M is a metal selected from the group consisting of silver, lead, mercury, gold, copper, zinc and cadmium. Z is a chalcogen selected from the group consisting of tellurium (Te) and a combination of selenium (Se) and tellurium (Te). R is an alkyl or aryl group such as phenyl, naphthyl, biphenyl, methyl, ethyl, propyl, butyl or pentyl.

Finally, in another embodiment is provided a device comprising a metal-organic chalcogenide composition according to Formula I: [M-Z-R]$_\infty$. M is a metal selected from the group consisting of silver (Ag), lead (Pb), mercury (Hg), gold (Au), copper (Cu), zinc (Zn) and cadmium (Cd). Z is a chalcogen selected from the group consisting of sulfur (S), selenium (Se), tellurium (Te) and combinations thereof. R is an alkyl or aryl group such as phenyl, naphthyl, biphenyl, methyl, ethyl, propyl, butyl or pentyl.

BRIEF DESCRIPTION OF THE DRAWINGS

The above and other features of the present disclosure, their nature, and various advantages will become more apparent upon consideration of the following detailed description, taken in conjunction with the accompanying drawings, in which.

Figure 7:
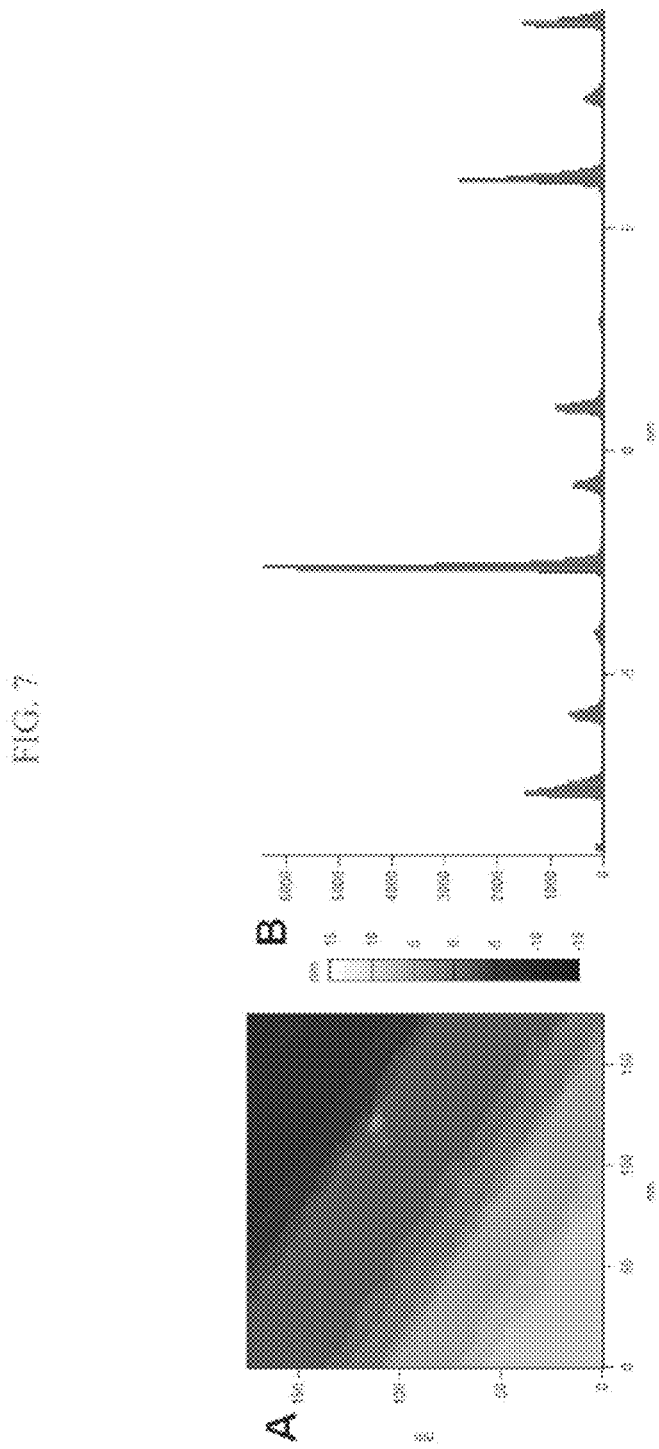
Figure 8:
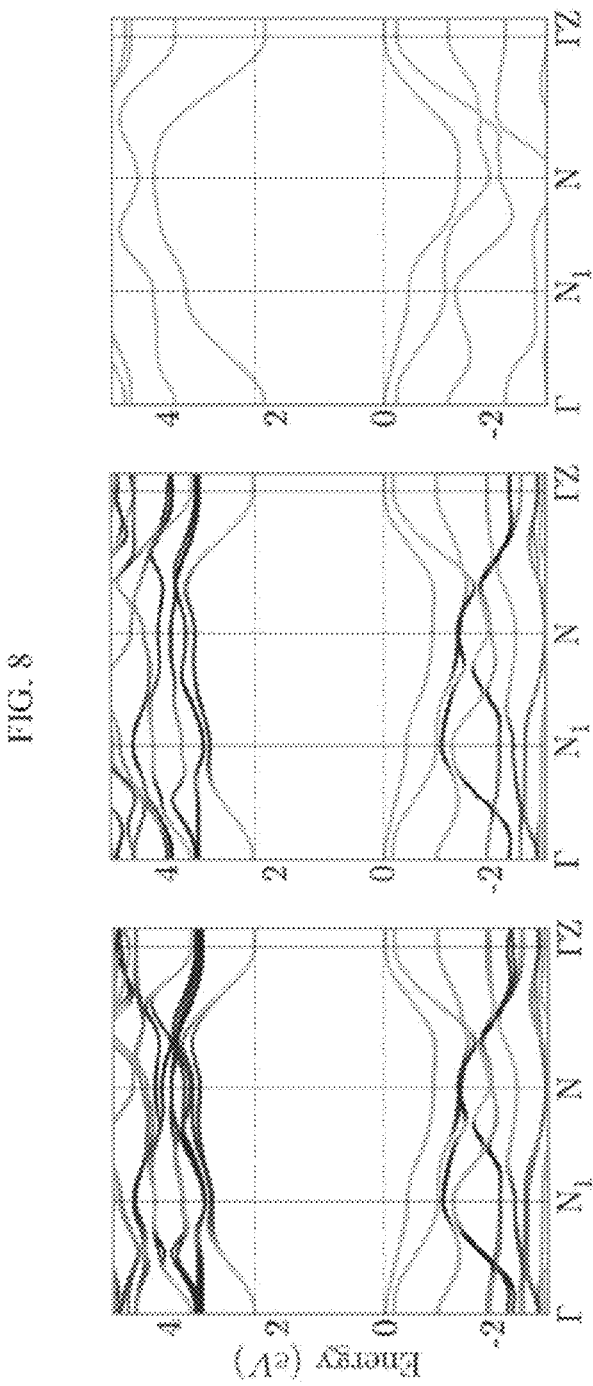
Figure 9:
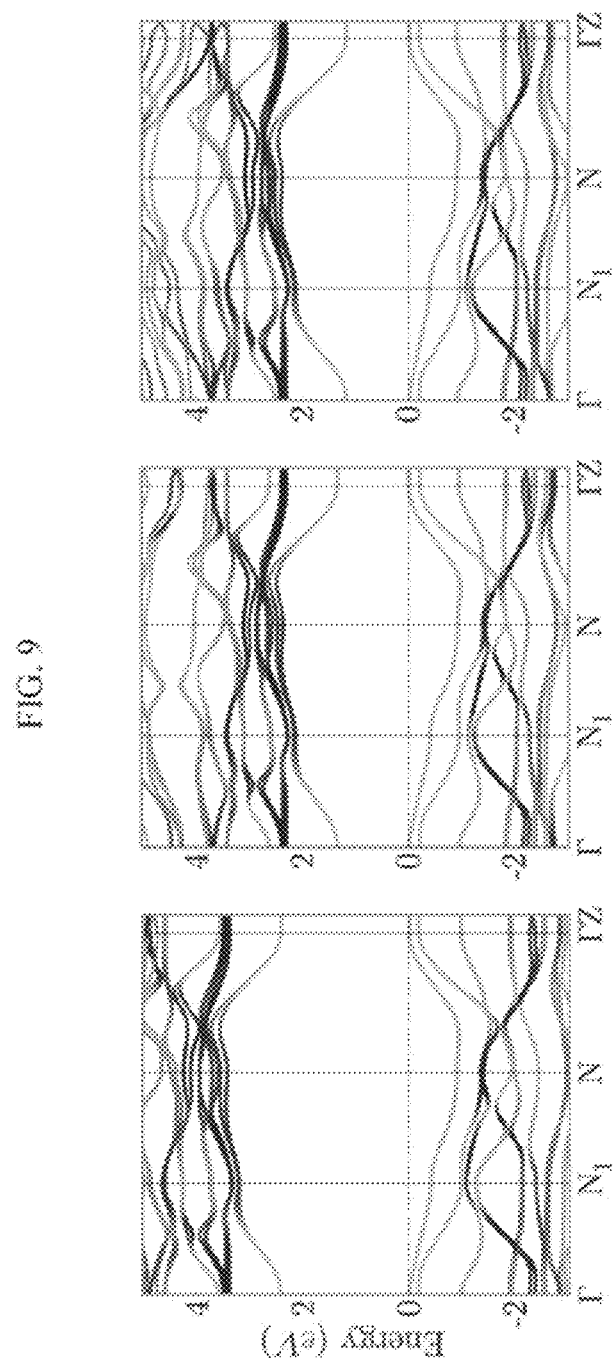
Figure 10:
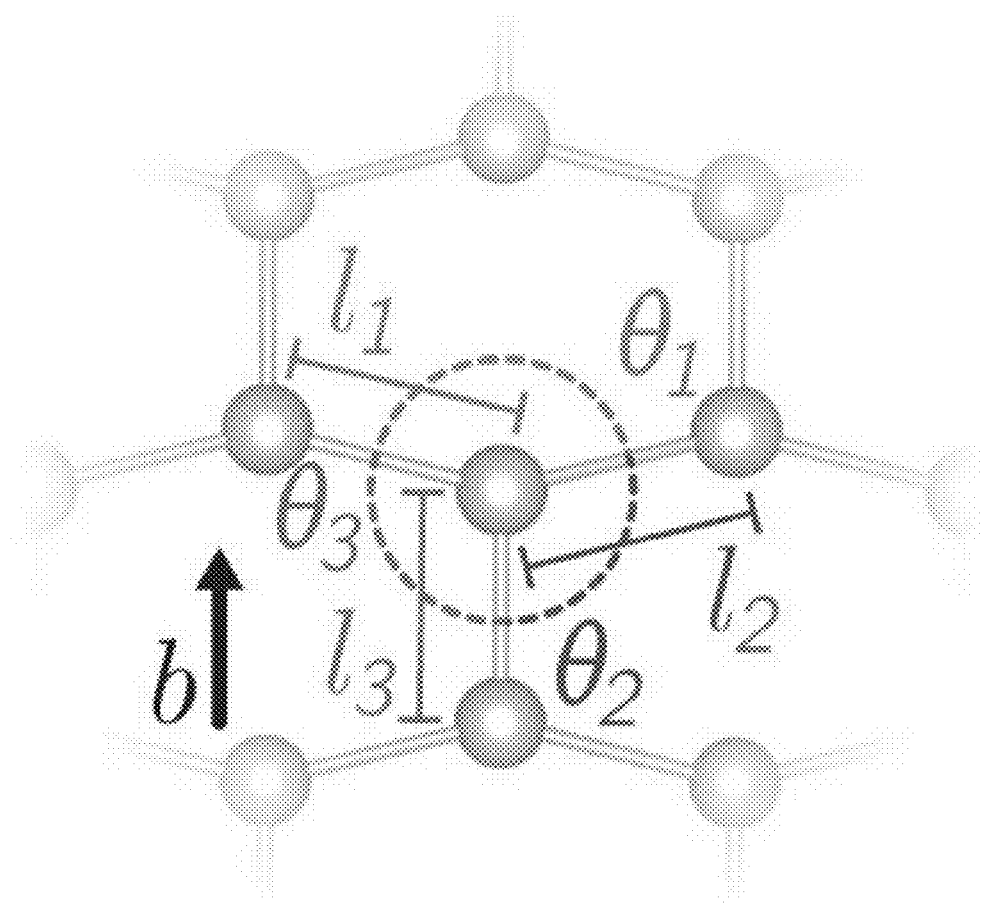
Figure 11:
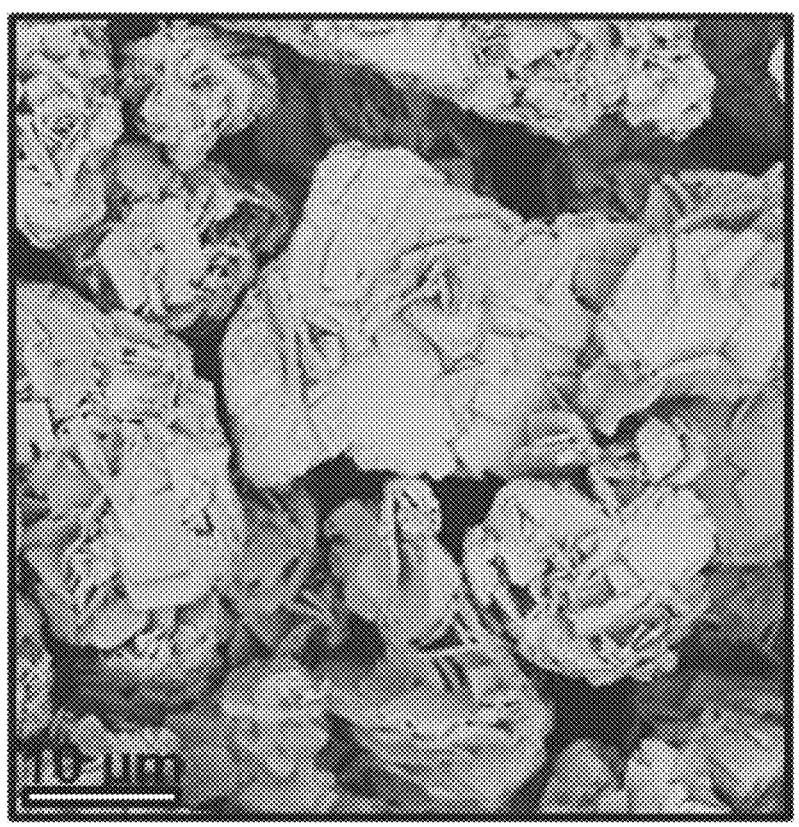
Figure 12:
Figure 14:
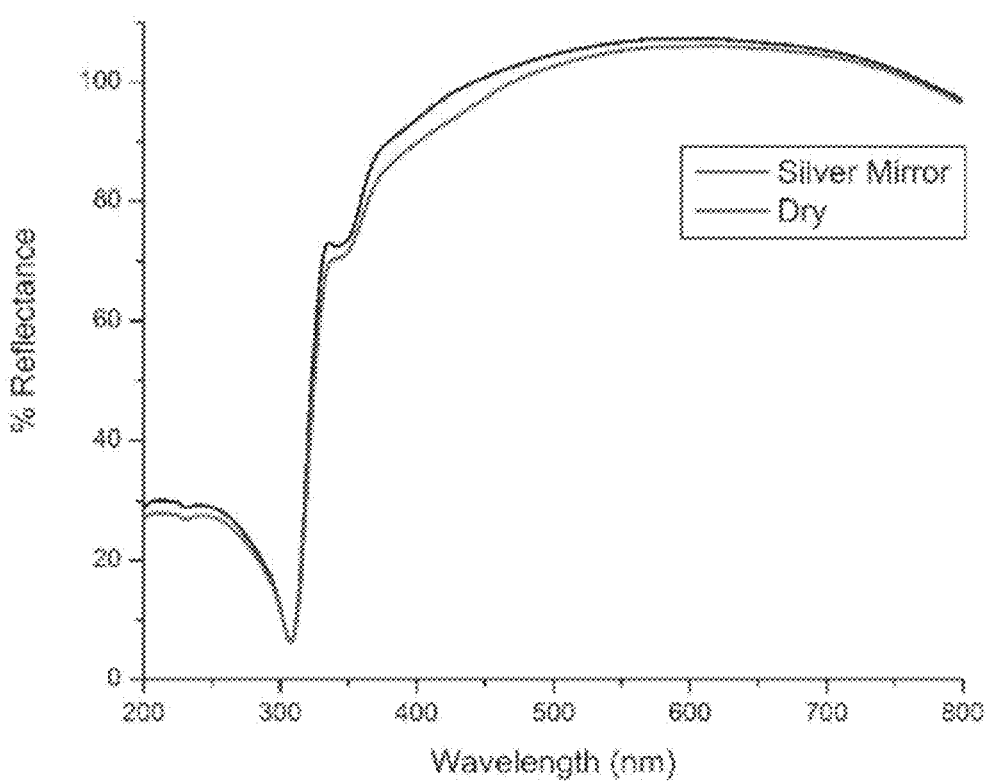
Figure 16:
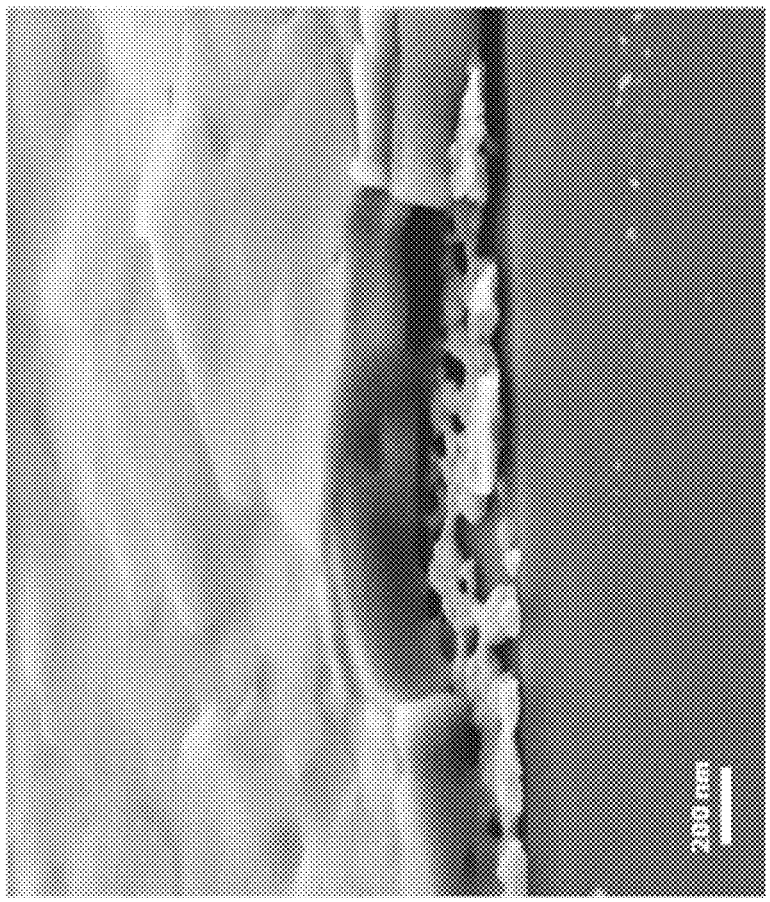
Figure 19:
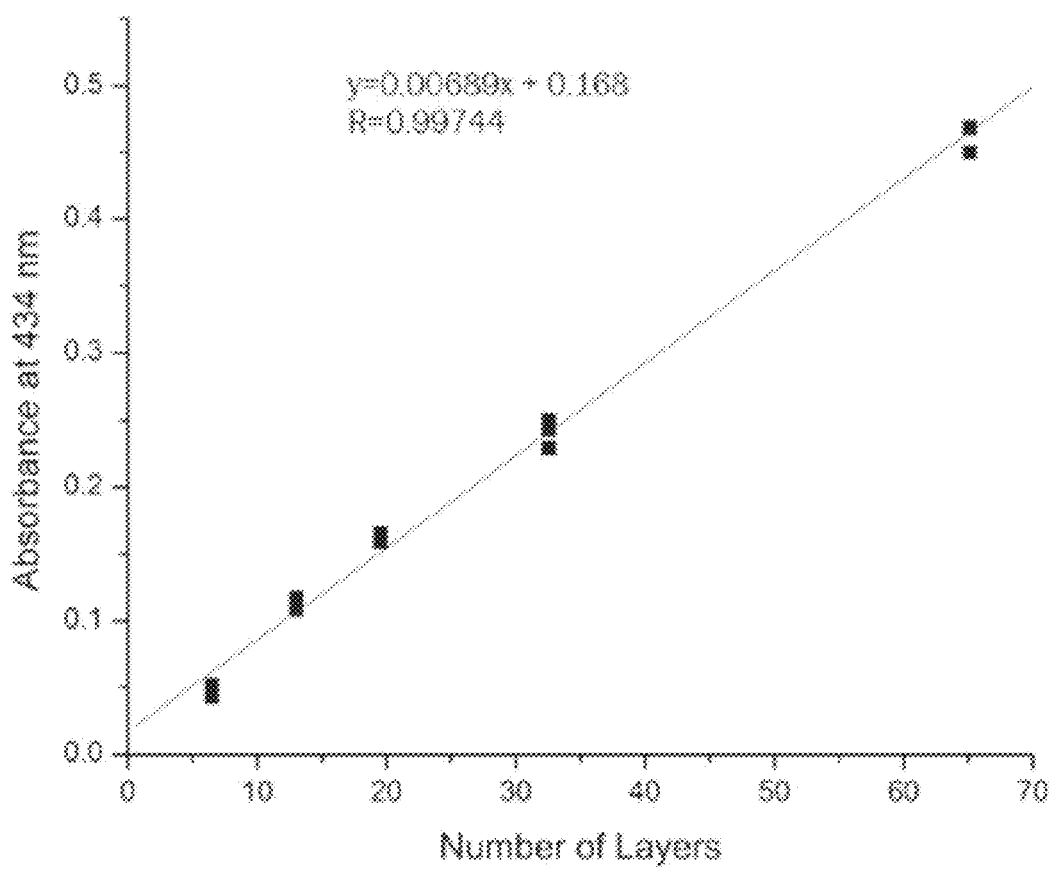
Figure 20:
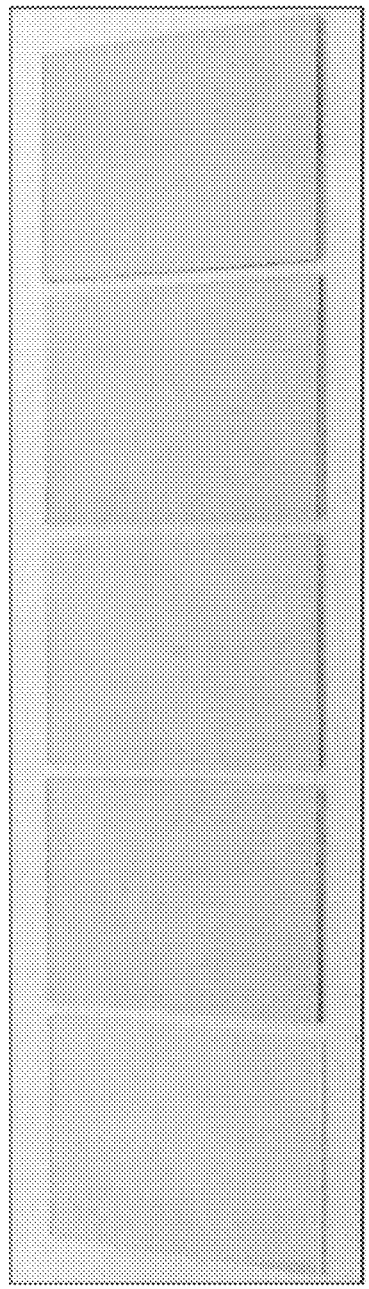
Figure 21:
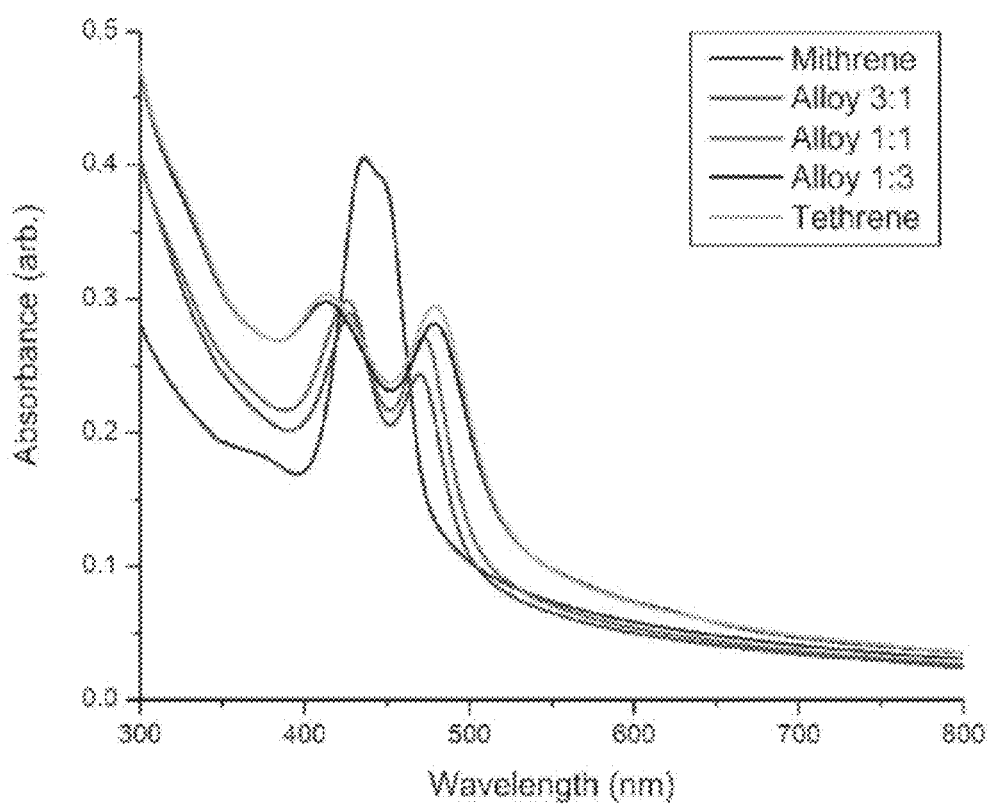
Figure 22:
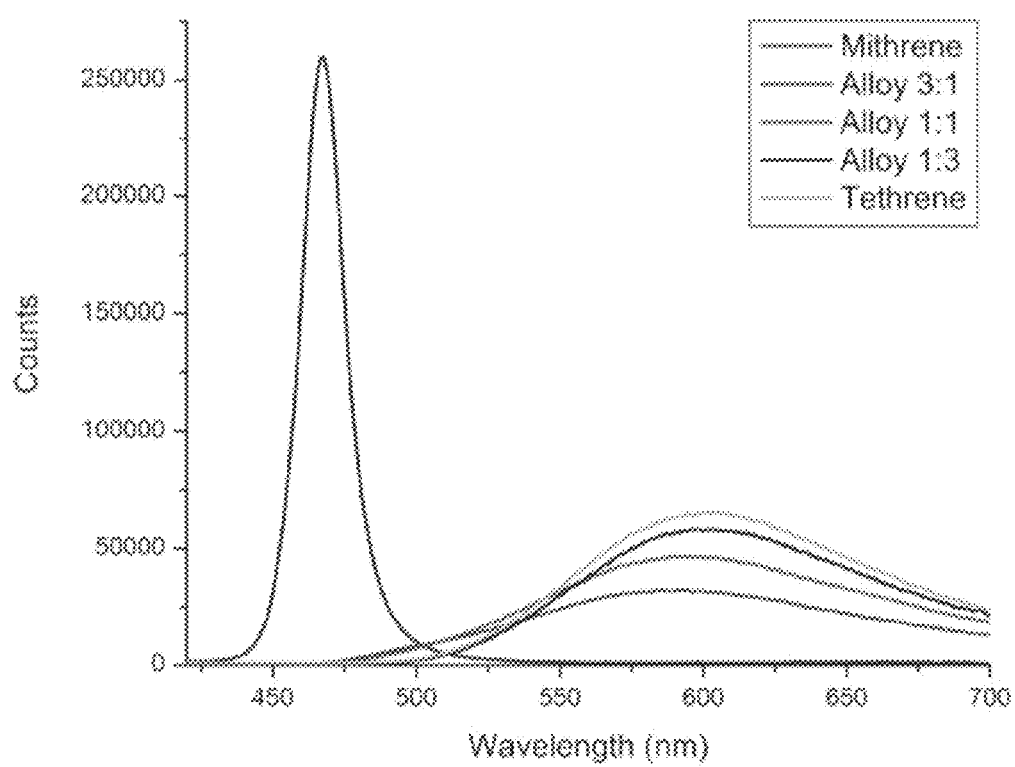
Figure 23:
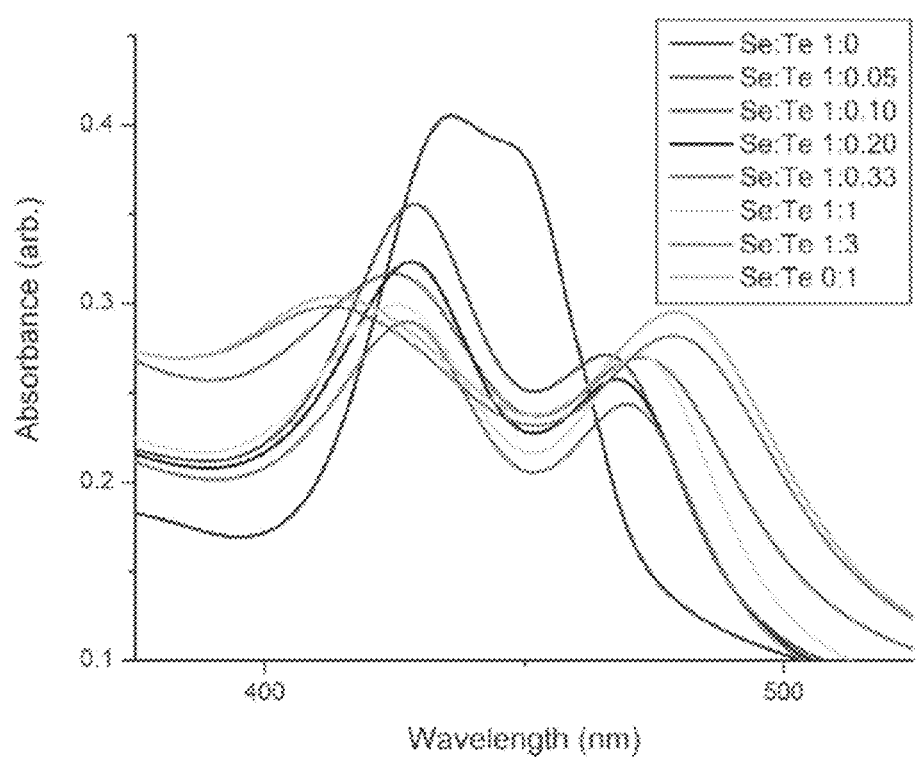
Figure 24:
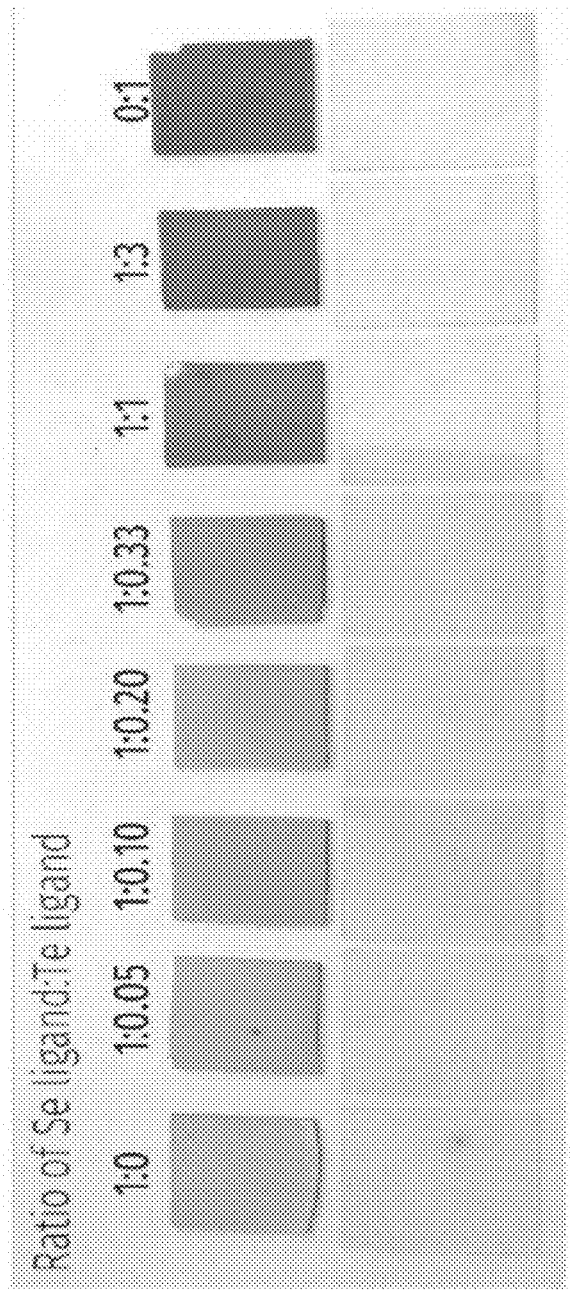
Figure 25:
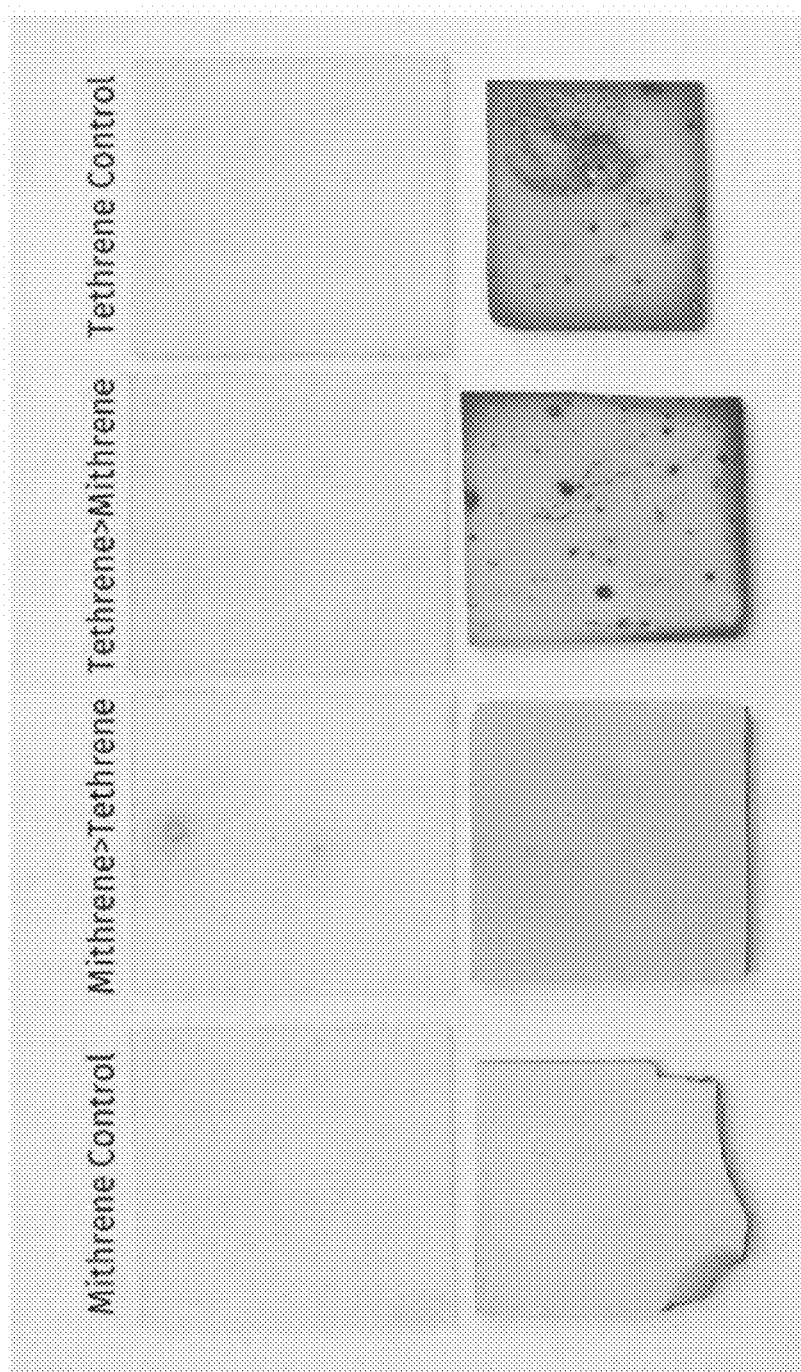
Figure 26:
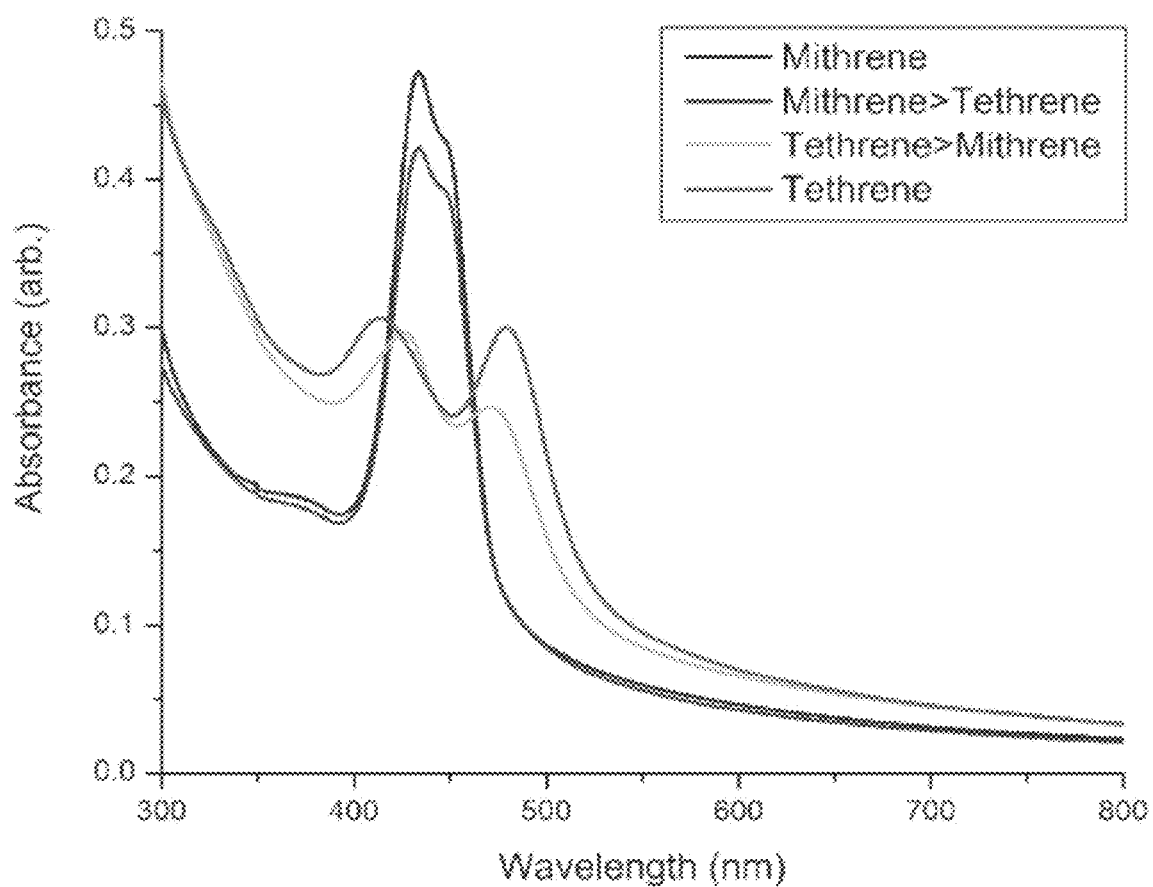

Fluorescence scanning confocal images of several individual crystals showing the near same size. The image is false colored to reflect the color of the emission wavelength, b) Distribution of the intensity from 157 individual crystals plotted as a function of the area of the crystal and c) aspect ratio. The Pearson's r-value for each set of data was calculated by using linear least squares fitting (solid line); for both the plots of area (r-value o 0.07) and aspect ratio (r-value of 0.1) the Pearson's r-values indicate little or no correlation with intensity. d) The normalized emission spectra of the 157 single crystals show the same peak intensity centered at 467 nm;

FIG. 7a is an atomic force micrograph of $[AgSePh]_\infty$ recorded in topography mode of step edges on a (001) silver benzeneselenolate crystal;

FIG. 7b is a histogram of FIG. 7a, revealing 11 step edges separated by 1.4 nm;

FIG. 8 is an illustration of the HSE band structures for bulk and single-layer $[AgSePh]_\infty$ and single layer $[AgSePh]_\infty$ with the phenyls replaced with hydrogens. Dashed lines show the Fermi level (at 0 eV) and the HSE band gap for bulk and single-layer $[AgSePh]_\infty$. Color of band signifies the fraction of band occupations by inorganic atoms (Ag and Se) versus organic atoms (C and H). Bulk and single layer USE hand structures look identical. Single layer and hydrogen truncated AgSe look similar for Ag and Se dominated hands with small changes to the band gap and mobility. The band structures is nearly identical between bulk and single layer $[AgSePh]_\infty$. The inorganic hands still present in $[AgSePh]_\infty$ replaced with hydrogens are similar to those of bulk and single layer $[AgSePh]_\infty$ with small changes to the band gap and effective masses at the direct gap;

FIG. 9 is an illustration of the HSE, PBF, and df2 hand structures for bulk $[AgSePh]_\infty$. Dashed lines show the Fermi level. Color of band signifies the fraction of band occupations by inorganic atoms (Ag and Se) versus organic atoms (C and H). Band occupations and shape remain similar across these three levels of theory. N, N_1 and Z are along the primitive lattice vectors a*, b* and c*, respectively;

FIG. 10 is an illustration of the parameters of the Ag lattice used in the relaxation table;

FIG. 11 is a micrograph of the larger crystals as recovered from the gram-scale, solution-phase synthetic route, obtained in near quantitative yield;

FIG. 12 is a photograph depicting the standard chemical deposition setup;

FIGS. 13a-d are a photographs depicting the results of the humidity study. a) Sample grown in humid air, b) Sample grown in ambient air, c) Sample grown in dry air, d) blank silver mirror;

FIG. 14 is a graphic illustration of the diffuse reflectance of a 200 nm thick silver mirror and a 100 nm thick silver sample tarnished in a dry atmosphere;

FIGS. 15a-c are photographs depicting the results of the oxygen study. a) Blank silver mirror, b) Sample tarnished inside the glovebox for two days, c) Control sample tarnished in ambient conditions for two days;

FIG. 16 is an SEM micrograph of a time sample. Light-colored patchy lattice is the silver layer; material above is $[AgSePh]_\infty$ material;

FIGS. 17a-c are graphic illustrations of the results of a time study of mithrene formation on 200 nm Ag+5 nm Ti on silicon wafers. a) photograph of entire time study sequence, b) SEM of surface of 1-day sample, c) SEM of surface of 8-day sample;

FIGS. 18a-b are graphic illustrations of various thicknesses of silver and mithrene. a) photograph of thickness series. Top: glass coated with different thicknesses of silver. Bottom: Different thicknesses of mithrene grown on glass (2 days, 80° C.). b) UV vis absorption of 3 runs of each thickness;

FIG. 19 is a Beer's Law plot of mithrene absorption per layer;

FIG. 20 is a photograph of films grown with varying ratios of diphenyl diselenide to diphenyl ditelluride. From left to riqht: 1:0 (mithrene), 3:1 (alloy), 1:1 (alloy), 1:3 (alloy), 0:1 (tethrene);

FIG. 21 is a UV-vis spectrum of alloy films; exciton peaks become farther apart and more tethrene-like as diphenyl ditelluride content increases;

FIG. 22 is an illustration of the photoluminescence of alloy films; peaks redshift and increase in intensity as diphenyl ditelluride content increases;

FIG. 23 is the UV-vis absorption spectrum of both alloy experiments. The samples made with smaller amounts of tellurium ligand further visualize the trend from mithrene to tethrene but show that tellurium effects still dominate even at very low loadings. The 1:0.10 sample appears to be an outlier;

FIG. 24 are photographs of silicon (top) and glass (bottom) alloy samples. Samples became both more orange and more matte (in the case of the silicon samples) as the amount of tellurium ligand increased. The more-orange 1:0.10 sample appears to be an outlier in terms of tellurium content, as confirmed by the absorption spectra;

FIG. 25 is a graphic illustration of the results of the transchalcogenation experiment. Top: glass substrates; bottom: silicon substrates. From left to right, mithrene control, mithrene>tethrene experiment, tethrene >mithrene experiment, tethrene control;

FIG. 26 is a UV-vis absorption spectrum of the glass samples from the transchalcogenation series;

FIG. 27a is an SEM image of a transehaleogenation sample, mithrene>tethrene; and FIG. 27b is an SEM image of a transchaleogenation sample, tethrene>mithrene.

DETAILED DESCRIPTION

The present disclosure generally provides compositions of bulk nanomaterials based on metal chalcogenolates, methods for the preparation thereof and devices and uses thereof.

The use of the terms "a," "an," "the," and similar referents in the context of describing the materials and methods discussed herein (especially in the context of the following claims) are to be construed to cover both the singular and the plural, unless otherwise indicated herein or dearly contradicted by context. Recitation of ranges of values herein are merely intended to serve as a shorthand method of referring individually to each separate value failing within the range, unless otherwise indicated herein, and each separate value is incorporated into the specification as if it were individually recited herein. The term "about" used throughout this specification is used to describe and account for small fluctuations. For example, the term "about" can refer to less than or equal to ±5%, such as less than or equal to ±2%, less than or equal to ±1%, less than or equal to ±0.5%, less than or equal less than or equal to ±0.1% or less than or equal to ±0.05%. All numeric values herein are modified by the term "about," whether or not explicitly indicated. A value modified by the term "about" of course includes the specific value. For instance, "about 5.0" must include 5.0.

All methods described herein can he performed in any suitable order unless otherwise indicated herein or otherwise clearly contradicted by context. The use of any and all examples, or exemplary language (e.g., "such as") provided herein, is intended merely to better illuminate the materials and methods and does not pose a limitation on the scope unless otherwise claimed. No language in the specification should be construed as indicating any non-claimed element as essential to the practice of the disclosed materials and methods.

"Chaleogenide" as used herein refers to a compound containing a chalcogen.

"Chalcogen" as used herein refers to an element of the periodic table from Group VI (i.e., sulfur, selenium, tellurium).

"MOCHA" as used herein, refers to a metal-organic chalcogenide assembly, and is a general material class for any crystalline assembly of hybrid coordination polymers.

"Mithrene" as used herein refers to the specific MOCHA, silver benzeneselenolate. Mithrene is a semiconducting material that retains 2D electronic properties in bulk multilayers. It is an air-stable metal-organic crystal comprised of ultrathin, conductive polymeric silver selenide layers, decoupled (insulated) by covalently linked organic spacers. Carriers are delocalized in the conduction bands. individual layers are electrically insulated by the organic ligands, producing a direct band gap semiconductor that exhibits intense blue fluorescence at 467 nm, and requires no physical exfoliation to exhibit its 2D properties. The insulating organic layers ensure that the transition-metal dichalcogenide (TMD)-like silver selenolate layers retain their 2-D properties and make it possible to build stacks of self-assembling mithrene that appear like a bulk material but act as semiconducting monolayers. Ab initio calculations confirm that the layers in the bulk crystal are direct band gap semiconductors and electrically isolated. Van der Waals (vdW) interactions between the arene rings hold the layers together in 3D.

Figure 1:
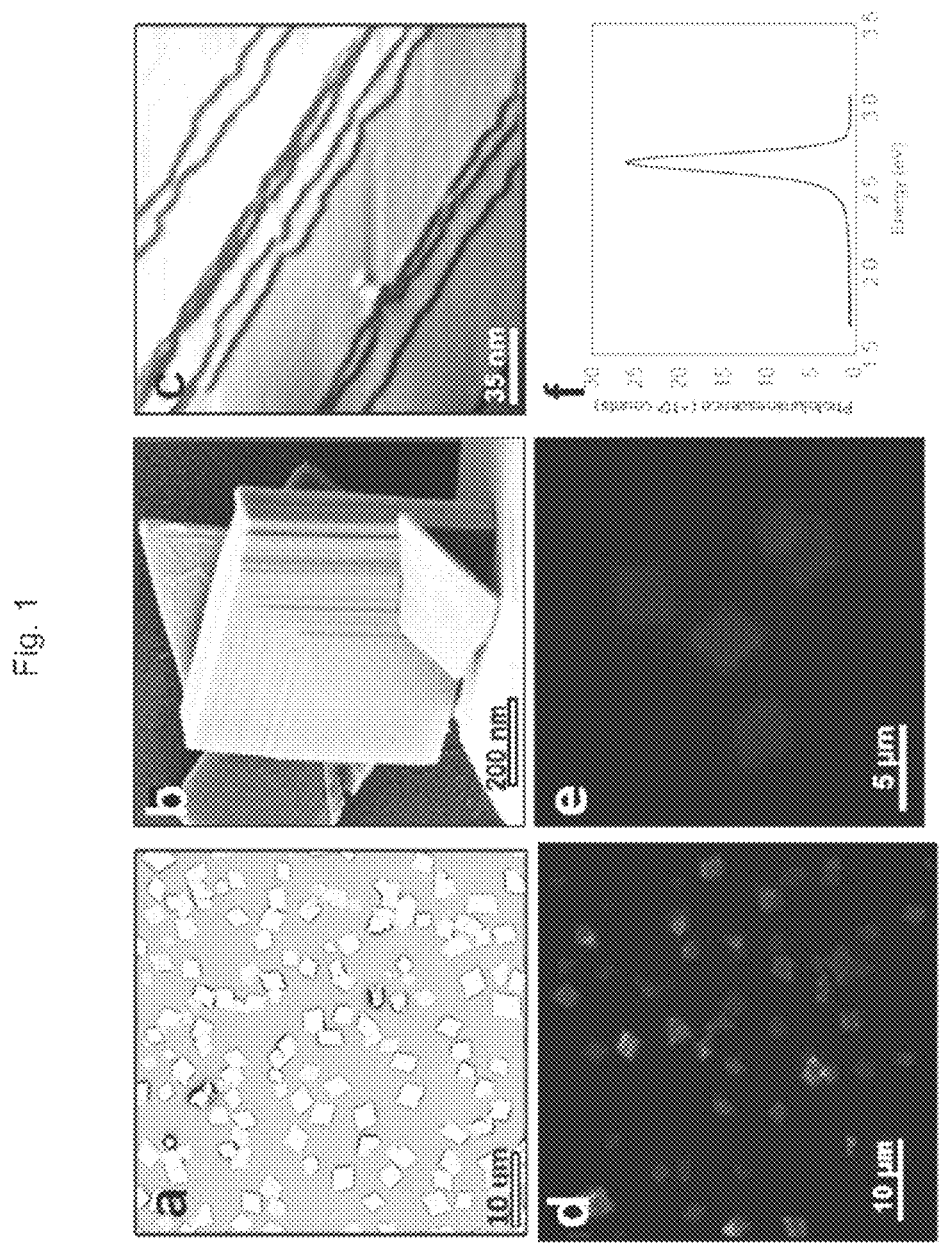
FIGS. 1a-f are images and emission spectrum of silver benzeneselenolate. a) Silver benzeneselenolate crystals recovered from the immiscible liquid-liquid interface of organic and aqueous solutions of diphenyl diselenide and silver nitrate, respectively. Crystals of [AgSePh]$_\infty$ have edge lengths between 1 and 4 microns. b) Scanning electron micrograph of a silver benzeneselenolate silver crystal reveals the layered structure of the crystal. Each layer is comprised of a 2D inorganic silver selenolate polymer, uniformly functionalized at every selenium site with a benzene ring. c) Atomic force microscopy reveals highly uniform [AgSePh]$_\infty$ (001) terraces with measured step heights at 1.4 nm. d,e) Confocal micrographs showing the color uniformity of photoluminescence in [AgSePh]$_\infty$. f) A single, intense emission of the solid at 467 nm is attributed to a direct-gap electronic transition.
Figure 5:
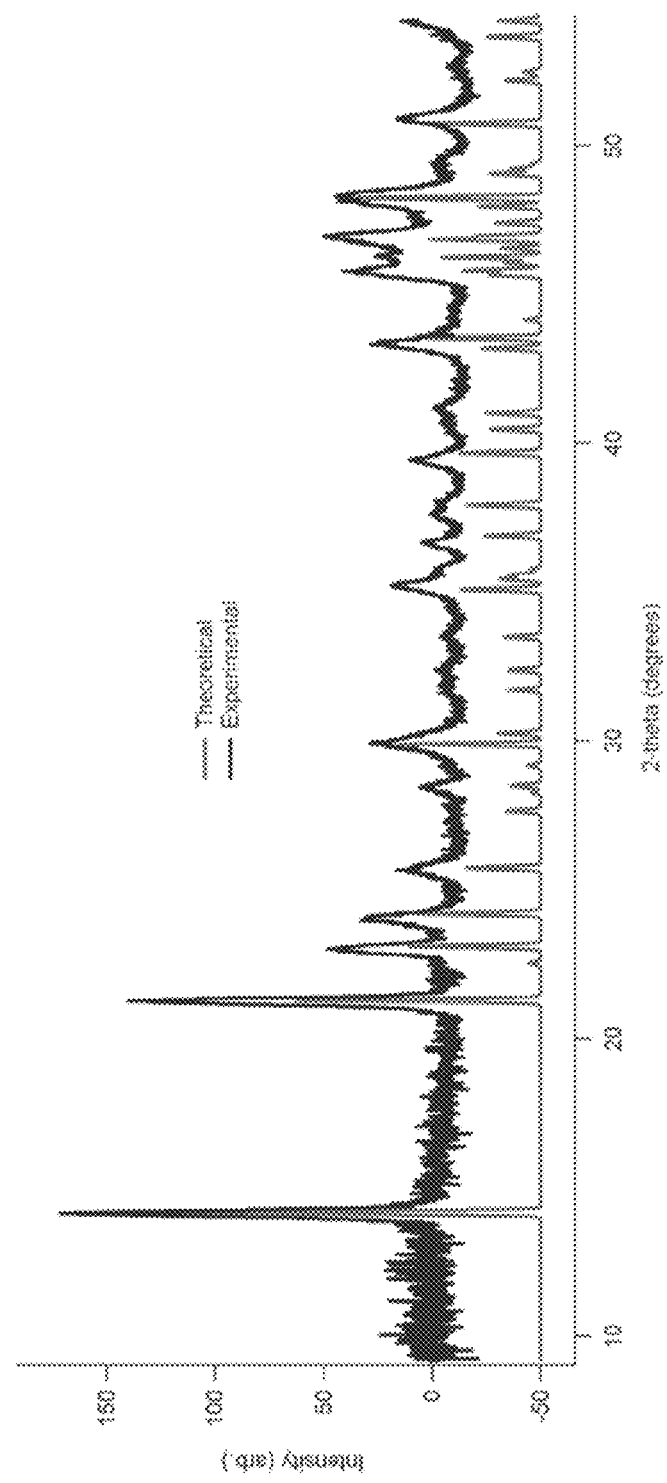
FIG. 5 is a powder X-Ray diffractogram of [AgSePh]$_\infty$ overlapping the diffractogram calculated from Cuthbert et at and providing positive identification for silver benzeneselenolate.

When prepared according to the methods disclosed herein, upon harvesting, the mithrene precipitate film appears non-crystalline; however, the film is comprised of lamellar, diamond shaped crystals of $[AgSePh]_\infty$, ranging 1-5 microns in size, shown in FIG. 1. The prominent (001) plane of the silver benzeneselenolate crystal is visible as the large flat face of the crystallites in FIGS. 1a-c. The smaller faces of the crystals are the (010) and (100) facets, the edges of a 2D hybrid crystalline polymer. Scanning electron microscopy resolves the individual molecular step edges, corresponding to the thickness of a single silver benzeneselenolate sheet. Atomic force microscopy (AFM) confirms the expected 1.4 am step height of the (001) crystal plane. The molecular terraces are largely defect free over hundreds of nanometers. We confirmed the structure by matching the powder X-Ray diffiactogram to the theoretical pattern (FIG. 5).

Figure 2:
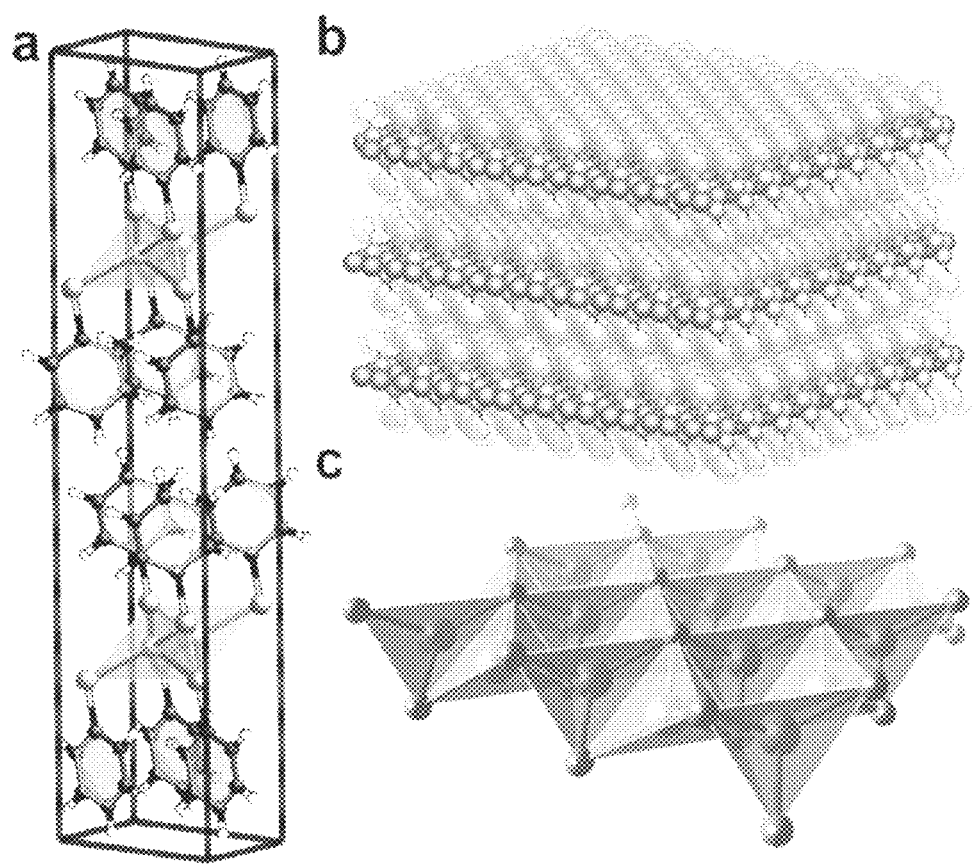
FIGS. 2a-c are illustrations of the single crystal structure of silver benzeneselenolate. a) The monoclinic unit cell of solid silver benzeneselenolate contains two complete layers of hybrid metal-organic 2D polymer. Silver is coordinated tetrahedrally by four selenium atoms. b) The multilayered structure electrically isolates inorganic layers via the benzene moieties oriented above and below the silver monolayer. c) Each silver atom has four coordinating selenium atoms in a distorted tetrahedral configuration with three argentophillic Ag-Ag interactions. Silver is represented as the grey spheres, selenium in dark orange, and carbon in black. Aromatic rings are accented in blue.
Figure 6:
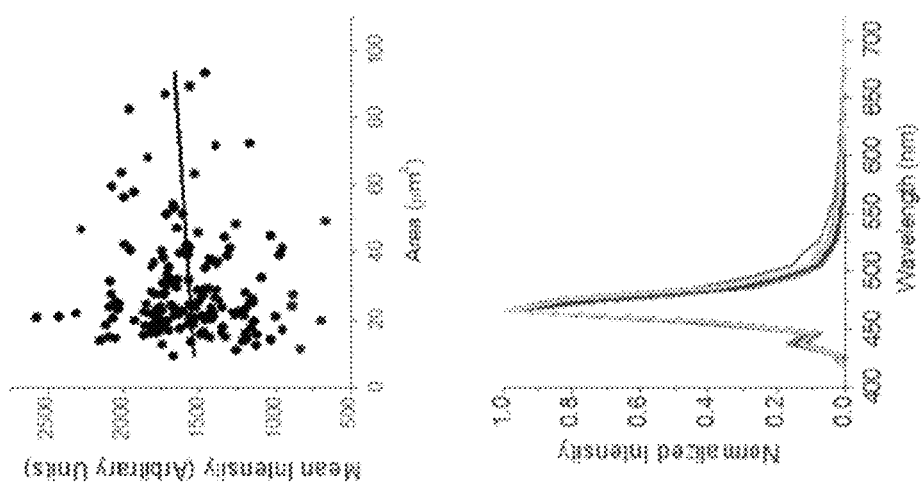
FIGS. 6a-d are illustrations of the results of fluorescence emission intensity studies of [AgSePh]$_\infty$. The fluorescence emission intensity of single crystals shows little variation, a)
Figure 6:
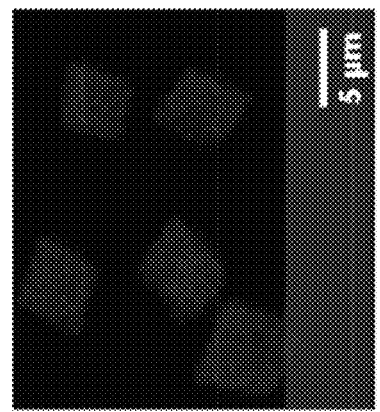
Figure 6:
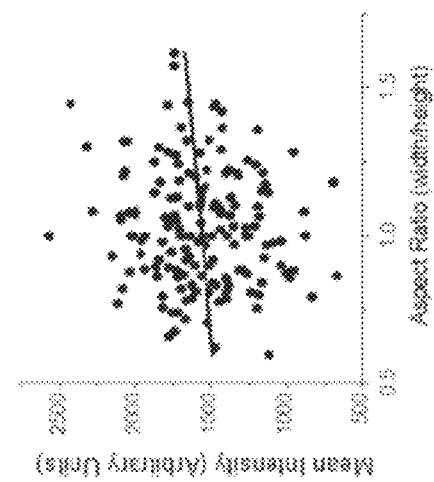

Layers of $[AgSePh]_\infty$ are stacked such that each consecutive layer is shifted relative to one another, described by a monoclinic unit cell with an angle of 96 degrees within monoclinic space group 15 (C2/c), seen in FIG. 2. Each layer consists of an inner ultrathin AgSe layer bound by an outer unsaturated hydrocarbon shell, in the 2D inorganic sheet, silver atoms are coordinated by distorted tetrahedra of four selenium atoms, with each tetrahedron sharing 4 of its 6 edges with neighboring tetrahedra. The silver atoms form a hexagonal lattice that is stretched along the a axis. Ag—Ag separations are 2.911-3.029 Å, consistent with the distances observed in complexes exhibiting argentophilic metal-metal interactions. Ag—Se distances are 2.694-2.781Å, and the shortest Se . . . Se contacts are 3.409 Å between adjacent PhSe. Each selenium atom is additionally bonded to a phenyl either above or below the ultrathin AgSe layer. Between layers, the phenyl groups are oriented parallel to one another to sterically maximize the distance between the ligands. The benzene ring centroid-to-centroid distance was 4.68 Å. A 1.4 nm interlayer spacing between the planar inorganic phase is imposed by the crystalline arrangement of phenyl rings. The effect is nearly perfect electrical isolation between stacks of 2-dimensional sheets formed by the dielectric crystalline organic supramolecular assembly. This is therefore a supramolecular 2D quantum well stack, Noted are comparisons to two-dimensional TMDs, such as $MoS_2$, with some important distinctions due to the presence of the intervening organic groups and metal-metal interactions. $MoS_2$ is a layered indirect band gap semiconductor in the bulk, but has a direct band gap and high charge carrier mobility as a single layer. Similar to TMD van der Waals (vdW) solids, adjacent 2D layers of silver benzeneselenolate are covalently decoupled. Unlike the TMD solids, the vdW coupling is strongest between the organic ligands, rather than between neighboring AgSe planes. As the transition metal chalcogenide layer is chemically and electrically decoupled from its neighboring layers, the bulk hybrid silver benzeneselenolate system might be expected to exhibit properties more associated with monolayer-TMDs than with hulk-TMD systems. To test this hypothesis, we measured the photoluminescence (PL) spectroscopically and microscopically, and the results are shown in FIG. 1. On excitation with shorter wavelength light, a single PL peak is observed at 2.65 eV, or 467 nm, a deep blue (FIG. 1f). Confocal micrographs reveal the emission wavelength invariance with number of layers and crystal size. We observed no correlations between crystal aspect ratio or surface area and observed intensity or color (FIG. 6). $[AgSePh]_\infty$ is robust and can be stored as a dry solid or as a dispersion in isopropyl alcohol for >6 months. With exposure to air and natural light, the chartreuse color gains green undertones over a months' time; however, we still observed no change in emission wavelength.

Disclosed herein are two new, mild synthetic routes for forming mithrene as well as related crystalline polymers of metal organochalcogenates. Mithrene, and, more generally, metal organoehalcogenate crystalline polymers of the present invention, may be prepared using self assembly as the synthetic technique. Using metal-directed self-assembly, low-dimensional structures of metal-chalcogertides can be synthesized that otherwise form bulk, covalent crystals of disparate coordination geometry. Coordination polymerization of metals with orqanochalcogens is the driving force for a self-assembly reaction. The result is crystalline assembly of low-dimensional inorganic nanostructures.

Therefore, in one aspect of the present invention is provided a method of preparing a crystalline metal chalcogenide of Formula I: $[M-Z-Ar]_\infty$. The method comprises providing a first solution comprising a metal ion, $M^+$, in a first solvent, the metal ion obtained by dissolving a metal component, $M_pX_q$, in the first solvent; providing a second solution comprising a diaryl dichalcogenide, Ar-Z-Z-Ar, in a second solvent; and contacting the first solution with the second solution to provide the metal chalcogenide as a crystalline, bulk nanomaterial. The reactions occurring are represented by partial. Equations 1 and 2, wherein a metal ion M+ is produced in solution from the metal component and reacts with the diaryl dichalcomnide.

$$M_pX_q \rightarrow M^+ + X^+ \quad \text{(Eq. 1)}$$

$$M^+ + Ar\text{-}Z\text{-}Z\text{-}Ar \rightarrow [M\text{-}z\text{-}Ar]_\infty \quad \text{(Eq. 2)}$$

The metal (M), corresponding to the metal ion (M+), is selected from the group consisting of silver (Ag), lead (Pb), mercury (Hg), gold (Au), copper (Cu), zinc (Zn), tin (Sn), cobalt (Co), thallium (Tl), gallium (Ga), indium (In), and cadmium (Cd). In some embodiments, M is silver. p may be 1 or 2. X is selected from the group consisting of O, $NO_3$, $SO_4$, Cl, Br, $CH_3CO_2$, $CF_3SO_3$, $PF_6$, $BF_4$, and $ClO_4$. q may be 1, 2, or 3. One skilled in the art will recognize that other equally suitable species of X (i.e., counter ions) may he selected based on availability, solubility, cost, and other factors. For example, the metal component may be a salt of a metal, or an oxide of a metal, including, but not limited to, silver tetrafluoroborate ($AgBF_4$), zinc sulfate ($ZnSO_4$), silver oxide ($Ag_2O$ or AgO), copper oxide ($Cu_2O$ or CuO), thallium oxide ($Tl_2O_3$), and the like. In some embodiments, X is $NO_3$ (nitrate). In a preferred embodiment, $M_pX_q$ is $AgN)_3$ (silver nitrate: p=1, q=1). Ar-Z-Z-Ar represents a diaryl dichalcogenide. In some embodiments, Z is sulfur, selenium, tellurium, or combinations thereof. In some embodiments Ar is phenyl or naphthyl, In some embodiments, the diaryl dichalcogenide is diphenyl diselande. A diaryl dichalcogenide species is advantageously employed as the organochalcogen source as it is not strong-smelling and is effectively air-stable as compared to other related potential organochalcogen sources (i.e., Ar—Z—OH). In one embodiment, the diaryl dichalcogenide is diphenyl diselenide and the metal salt is silver nitrate. In this embodiment, the product is silver benzeneselenolate ($[Ag\text{-}Se\text{-}Ph]_\infty$, mithrene).

In some embodiments, the first solvent and the second solvent are selected so as to be immiscible. In this embodiment, the contacting of the first and second solutions occurs at the interface of the immiscible solvents. Formation of the crystalline metal chalcogenide occurs at this interface. Reductive cleavage of the dichalcogenide restricts the product precipitation to the liquid-liquid interface and crystallization occurs readily without stirring, manifesting as an opaque film between the two solvent layers. One skilled in the art will recognize that many suitable solvent pairings exist which may fulfill the requirements of immiscibility and suitable physical properties (polarity, boiling point, etc.), in some embodiments, the first solvent is water and the second solvent is an aromatic hydrocarbon. In some embodiments, the second solvent is toluene. The concentration of metal ion in the first solution may vary. In some embodiments, the concentration is about 0.1 mM to about 100 mM. In some embodiments, the concentration is about 3 mM. The concentration of diary(dichalcogenide in the second solution may vary, in some embodiments, the concentration is about 0.1 mM to about 100 mM. In some embodiments, the concentration is about 3 mM. The contacting may be performed for various durations of time. In some embodiments the contacting occurs over a period from about 1 to about 3 days. The contacting may be performed at various temperatures. In some embodiments, the contacting is performed at a temperature from about 0° C. to about 100° C. In some embodiments, the contacting is performed at a temperature of about 25° C. One skilled in the art will recognize that such variables as time, temperature and concentration may be varied and optimized for a particular reaction; such optimization remains within the scope of the present invention.

The resulting crystalline metal chalcogenide may be isolated from the interface of the two solutions by various methods. In some embodiments, the crystalline metal chaleogenide is recovered by adhering the crystalline material to a substrate. In some embodiments, the adhering is performed by passing the substrate through the liquid interface into the first solution, and withdrawing the substrate through the second solution. This may be performed at various angles. In some embodiments, the withdrawal of the substrate is performed at an angle of about 45 degrees. The substrate may be any non-hydrophobic material. In some embodiments, the substrate is glass or silicon.

The crystalline metal chalcogenide may also be isolated from the interface of the solutions by sequentially removing the solutions. In one embodiment, the crystalline metal chalcogenide is recovered by removing the first solution while retaining the crystalline material and the second solution, removing the second solution while retaining the crystalline material, and collecting the crystalline material. The resulting crystalline material may be further processed and/or purified. For example, the material may be suspended in a solvent such as isopropanol and subsequently pelletized by centrifugation. Removal of isopropanol and air drying of the resulting pellet provides the material in purified form.

Alternatively, the crystalline metal chalcogenides of the present invention may be prepared by a one-pot, gram-scale method based on the same reactions of Equations 1 and 2. In this embodiment, the crystalline product may be produced with dimensions in excess of tens of microns (FIG. 11). In this embodiment, the first and second solvents are miscible. In this embodiment, the contacting of the first and second solutions further comprises: a) adding a stabilizing ligand to the first solution with stiffing under an inert atmosphere: b) cooling the resulting solution; c) adding the second solution to the cold first solution with stirring; d) warming the resulting cold solution while stirring; e) diluting the warmed solution with a suitable dilution solvent while rapidly stirring until the mixture is clear and colorless; and f) collecting the crystalline product by decanting or filtering. In some embodiments, the first solvent and second solvent are independently selected from the group consisting of tetrahydrofuran, acetonitrile, dimethylsulfoxide, pyridine, chloroform, dichloromethane, benzene, toluene, and methanol. One skilled in the art will recognize and select appropriate solvents based on properties such as polarity and ability to solubilize the reaction components. In certain embodiments, the first solvent and second solvent are the same. In certain embodiments, the first solvent and second solvent are both tetrahydrofuran. One skilled in the art will recognize and select appropriate stabilizing ligands appropriate to the particular reaction being conducted. In some embodiments, the stabilizing ligand is a phosphine. In some embodiments, the stabilizing ligand is triphenylphosphine. One skilled in the art will recognize that this method may be conducted under a variety of conditions without departing from the spirit of the disclosed method, for example, at a variety of temperatures, for various periods of time, at various rates of addition, at various concentrations, with various speeds of stirring, and employing various solvents at each stage, In some embodiments, the first solution is cooled to a temperature from about −80° C. to about 0° C. In some embodiments, the solution in d) is warmed to a temperature from about 20° C. to about 30° C. In some embodiments, the dilution solvent is diethyl ether. In some embodiments, the dilution solvent is an aliphatic hydrocarbon, for example, hexane or pentane.

Crystalline metal organochalcogenides of the present invention may also be synthesized by a process very similar to that occurring in the tarnishing of metals. Tarnishing is a natural process brought about by atmospheric air, water, and pollutants corroding the surface of a metal. The mechanism and products of the tarnishing process vary depending on the atmospheric compounds reacting with the metal surface. With silver, for example, the most common tarnish is silver sulfide, which is caused by a reaction with hydrogen sulfide ($H_2S$). Many studies have sought to understand the tarnishing process in order to effectively protect or clean artifacts with silver surfaces. Although the nature of the tarnishing mechanism varies depending on the atmospheric pollutant reacting with the silver surface to form the tarnish, all research points to humidity (atmospheric water content) and oxygen as necessary components of the tarnishing process.

This centuries-old sulfur chemistry has been extended herein to other chalcogens to develop new ways to grow TMDs through self-assembled, tarnish-grown MOCHAs. Much like the tarnish that forms on antique silverware, methods are disclosed herein to introduce the organic precursor to the silver surface in the vapor phase. The principles of tarnishing were utilized to develop a simple technique for producing multi-centimeter-area films of semiconducting mithrene and tethrene (mithrene's tellurium-containing variant). This technique is performed at low temperatures within the range of any laboratory oven and uses simple molecular precursors to create large, robust films of bulk 2D semiconductors with tunable optical properties interesting for applications in optoelectronic devices such as photovoltaics. This tarnishing synthesis allows preparation of large-area samples of MOCHAs which indicate excitonic and direct-gap semiconducting properties. These large, uniform films of robust hybrid materials with tunable optical properties can potentially be used in optoelectronic devices such as solar cells.

Accordingly, in another aspect of the invention is provided a vapor phase deposition "tarnish" method of preparing a substrate coated with a film comprising a metal chalcogenide of Formula I: $[M-Z-R]_\infty$ (partial Equation 3).

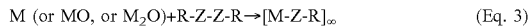

$$M \text{ (or MO, or } M_2O) + R\text{-}Z\text{-}Z\text{-}R \rightarrow [M\text{-}Z\text{-}R]_\infty \quad \text{(Eq. 3)}$$

The method comprises providing a substrate comprising a coating of metal (M) or an oxide thereof (i.e., MO, $M_2O$) and exposing the substrate coated with the metal or oxide thereof to a vapor phase comprising a first dialkyl car diaryl dichalcogenide $R_2Z_2$, for a time sufficient to provide a film of a first $[M-Z-R]_\infty$ on the substrate. in some embodiments, the metal M is selected from the group consisting of silver (Ag), titanium (Ti), zinc (Zn), lead (Pb), copper (Cu), indium (In), gallium (Ga) and cadmium (Cd). in certain embodiments, the metal is silver. In certain embodiments the coating is a metal oxide. In some embodiments, the metal oxide is a silver oxide or a copper oxide (for example, $Ag_2O$, AgO, $Cu_2$, CuO). In some embodiments, Z is sulfur (S) selenium (Se), tellurium (Te) or combinations thereof, In some embodiments, R is phenyl, naphthyl, biphenyl, methyl, ethyl, propyl, butyl or pentyl, in certain embodiments, M is silver, Z is selenium, and R is phenyl.

Figure 17:
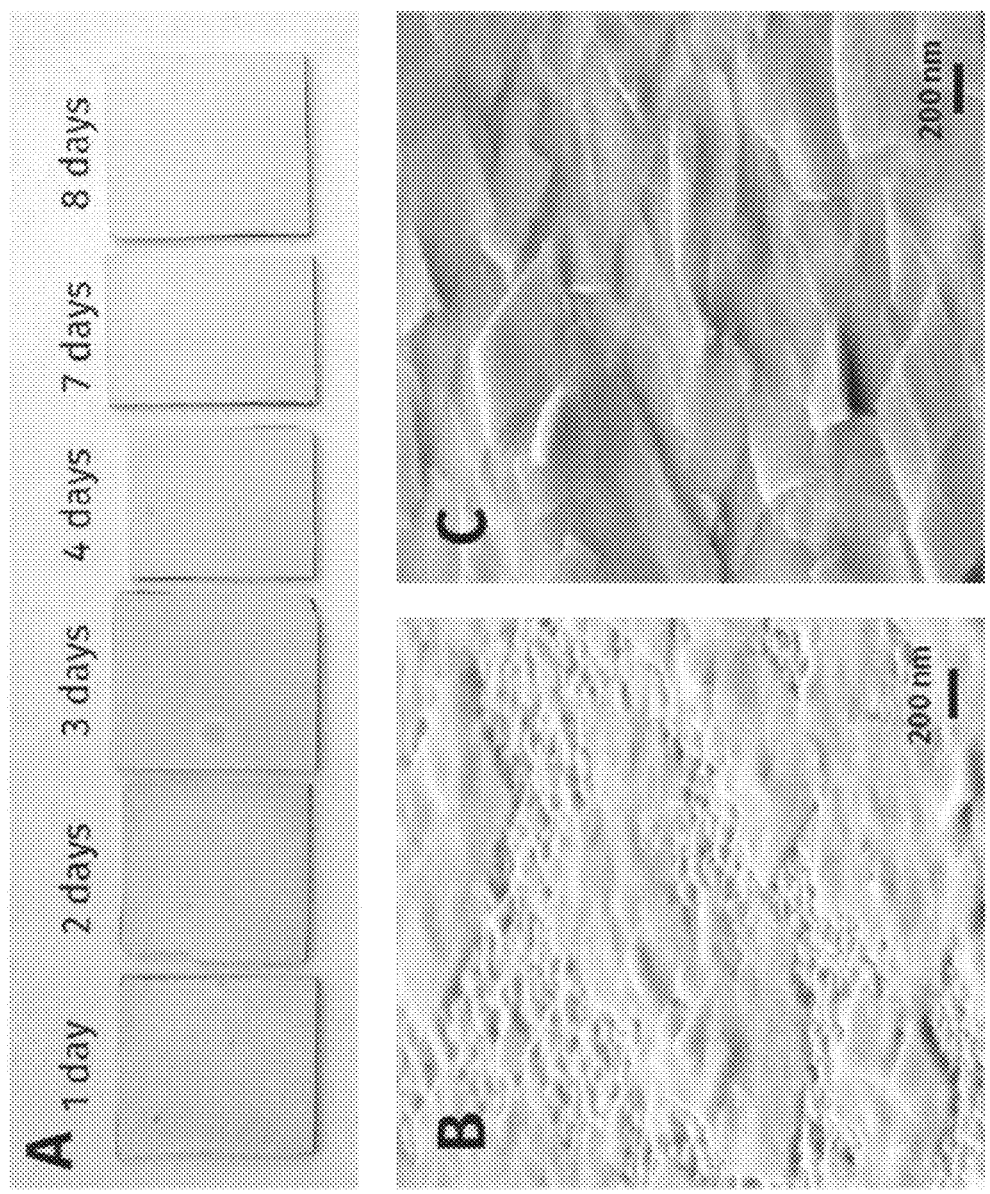

The time sufficient to provide the desired film may vary and will depend on reaction conditions (i.e., temperature, concentration of dichalcogenide, thickness of metal coating, etc.). In some embodiments, the time is from about 12 hours to about 14 days (FIGS. 16, 17). The temperature at which the exposing is conducted may vary. In some embodiments, the exposing is conducted at a temperature from about 25° C. to about 100° C. The substrate may vary according to purpose, and may be selected from a wide range of suitable materials and thicknesses. In certain embodiments, the substrate is glass, quartz, silicon or plastic. The thickness of the metal coating on the substrate can vary according to intended purpose, and may he prepared according to methods known in the art. In sonic embodiments, the coating of metal on the substrate is about 1 nm to about 100 nm in thickness. Thickness of the MOCHA layer may also be varied. See, for example, FIG. 18. The coating of metal may further comprise more than one layer, and each layer may be selected independently. This may be useful, for example, in improving adhesion. In some embodiments, the first layer comprises titanium and the second layer comprises silver. In some embodiments, the first layer is in contact with the substrate, while the second layer is dispersed over the first layer. Without wishing to be bound by theory, it is contemplated that the presence of varying quantities of moisture and oxygen may affect the rate and extent of tarnish formation (see FIGS. 13 and 15, respectively). Accordingly, in some embodiments, the vapor phase further comprises water, in certain embodiments, the vapor phase is saturated with water. Water vapor is provided by, for example, placing a container containing a measured amount of liquid water into a reaction vessel, along with the substrate and first dialkyl or diaryl dichalcogenide, and allowing the liquid water to evaporate into the atmosphere of the reaction vessel in which the vapor phase deposition reaction is being conducted. In some embodiments, the vapor phase further comprises oxygen.

In some embodiments, the method may utilize different chalcogenides to provide layered MOCHAs. Therefore, in some embodiments, the method further comprises exposing the substrate coated with a film of the first $[M-Z-R]_\infty$ to a second dialkyl or diaryl dichalcogenide, $R_2Z_2$, in the vapor phase for a time sufficient to provide a film of the second $[M-Z-R]_\infty$ on the substrate, wherein the first and second dialkyl or diaryl dichalcogenide are different, and the resulting first and second $[M-Z-R]_\infty$ are different, In certain embodiments, the film of the first $[M-Z-R]_\infty$ is $[Ag—Se—Ph]_\infty$ and the film of the second $[M-Z-R]_\infty$ is $[Ag—Te—Ph]_\infty$ ("tethrene"). In some embodiments, the substrate is simultaneously exposed to a mixture of different dialkyl and/or diaryl dichalcogenide to produce a mixed alloy. One skilled in the art will recognize that the relative concentrations of the first and second dialkyl or diaryl dichalcogenides may he varied to produce MOCHAs with varied ratios of chalcogenide, and, correspondingly, different properties. By alloying mithrene and tethrene, the absorption and emission properties of the resulting MOCHA material may be varied. See, for example, spectra and photographs in FIGS. 20 to 27.

In a further aspect of the invention are provided novel metal-organic chalcogenide compositions according to Formula $[M-Z-R]_\infty$, wherein M is selected from the group consisting of silver, lead, mercury, gold, copper, zinc and cadmium; Z is selected from the group consisting of tellurium and a combination of selenium and tellurium; and R is phenyl, naphthyl, biphenyl, methyl, ethyl, propyl, butyl or pentyl. Such compositions may be prepared according to any of the methods disclosed herein. in some embodiments, such compositions are for use in a fluorescent resonance energy transfer (FRET) assay. In sonic embodiments, such compositions are for use as photocatalysts. In some embodiments, such compositions are for use in devices. In some embodiments, the device is a. semiconductor. In some embodiments, the device is a solar cell. in some embodiments, the device is a laser. In some embodiments, the device is a light-emitting diode (LED).

In a final aspect of the invention is provided a device comprising a metal-organic chalcogenide composition according to Formula I: [M-Z-R]$_\infty$, wherein M is selected from the group consisting of silver, lead, mercury, gold, copper, zinc and cadmium; Z is selected from the group consisting of sulfur, selenium, tellurium and combinations thereof; and R is phenyl, naphthyl, biphenyl, methyl, ethyl, propyl, butyl or pentyl. in some embodiments, the device is a semiconductor. In some embodiments, the device is a solar cell. In some embodiments, the device is a laser. In some embodiments, the device is a light-emitting diode (LED).

EXAMPLES

General

Standard high vacuum, Schlenk line technique was employed for gram scale synthesis under dried nitrogen atmosphere. All reagents were Obtained from commercial sources including dry toluene and tetrahydrofuran and were used without further purification. The reported yields are for isolated sample. Powder X-Ray diffraction studies were performed on a Bruker AXS D8 Discover GADDS X-Ray Diffractometer, operated at 35 kV and 40 mA at a wavelength of Co K$_a$, 1.79 Å. Scanning electron microscopy (SEM) images were collected on a Zeiss Gemini Ultra-55 Analytical Field Emission SEM and an FEL Phenol» G1 Tabletop SEM. UV-vis and diffuse reflectance spectra were taken on an Agilent Technologies Cary-5000 UV-Vis-NIR spectrophotometer. Photoluminescence spectra were taken on an Edinburgh Instruments FL980 Spectrometer.

Samples of crystalline silver benzeneselenolate specimens were prepared by the drop casting of isopropanol suspensions onto a silicon wafer, which were allowed to settle followed by drying the surface with a stream of compressed air. Specimens were coated with a thin layer of gold to prevent surface charging artifacts in electron microscopy as necessary.

Unless otherwise noted, chemicals were purchased from the distributor and used without further purification. Diphenyl diselenide and diphenyl ditelluride were purchased from TCI.

Crystalline silicon wafers were coated with silver to the specified thicknesses using an MBraun thermal evaporator within a nitrogen glovebox equipped with a Sigma Instruments SQC-310 deposition controller and quartz crystal microbalance; some wafers were first coated with a 5-7 nm titanium adhesion layer before being coated with silver.

Coverslips from VWR (1"×1", 0.17-0.25 mm thick) were used as the glass substrates. The quartz substrates (1"×1") were previously used for other experiments. They were washed and mechanically wiped with isopropyl alcohol, then were rinsed with first acetone, then isopropyl alcohol and dried with compressed air before being evaporated with silver.

Fluorescence Imaging Methods

Fluorescent images were acquired on a Zeiss LSM 710 confocal microscope with ate Axio Observer.Z1 (Carl Zeiss Microimaging, Thornwood, N.Y.), Crystalline [AgSePh]$_\infty$ was dried on glass coverslips (No. 1.5) and imaged using a 100× oil immersion objective (Plan-Apochromat, 1.40 NA). Confocal scans of the material were obtained using a 405 nm diode laser to excite the sample and a 585 µm wide pinhole. The emission spectrum was separated and the intensity of light between 400-700 nm (in 10 nm bins) was recorded on 32 detectors using the LSM 710 Linear Unmixing mode. The 32 images were imported to and analyzed using FIJI. Isolated crystals were defined using the tracing tool in FIJI to detect the edges of the single crystal and then used create a region of interest (ROI) around the crystal. For each ROI, the mean intensity, area, width and height was measured and recorded. Data were then exported to Origin 8.5.1. (Origintab, Northampton, Mass.) for analysis by linear regression and plotting.

Atomic Force Microscopy

AFM images were captured on a Cypher ES (Oxford Instruments). A budget Sensors TAP150G cantilever with a spring constant of 4.5 N/m was used in the repulsive tapping regime with an amplitude of 1.6 nm and a A$_{sp}$/A$_0$=0.08. The z sensor was calibrated using an 18 nm step sample. Unannotated micrograph and histogram showing step edges is found in FIG. 7.

Calculation Details

Density functional theory (DFT) calculations were performed using a plane-wave basis with the Vienna Ab Initio Simulations Package (VASP). We used a short-range hybrid functional of Heyd etc (HSE) for band structure calculations and LDA, used the generalized gradient approximation of Perdew. etc (PBE); and the vdW-df2 functional to relax the experimental structure electron-ion interactions are treated with PAW pseudopotential with a 520 eV plane-wave cutoff; and the Brillouin zone was sampled with a Monkhorst-Pack mesh of 15×15×3 for PBE and df2 relaxations and 7×7×1 for the computationally-more-demanding HSE calculations.

Two symmetrically equivalent configurations of the benzene ligands are possible within the C2/c space group for the given refinement of [AgSePh]$_\infty$. We calculated that the two orientations differ in formation energy by 214 meV per formula unit with DFT-PBE and we use the lower energy structure for DFT-HSE calculations. Despite the energy difference, the band structures of these configurations are nearly indistinguishable. We calculated the electronic structure for the average of these two configurations and also observed that the band structure remained largely unaffected by change in the ligands orientation. The structural parameters for the configuration used for our OFT calculations are given in FIG. 10. The CIF for the original refinement containing both configurations as partial occupancies can be found in Cuthbert et at.

DFT calculations were performed for bulk and single-layer [AgSePh]$_\infty$ in the lower energy of the two refined configurations (as described above) and single layer [AgSePh]$_\infty$ with the phenyls replaced with hydrogens. The hydrogens positions for the latter case are relaxed with DFT-PBE. The primitive cell was used for all calculations.

The structure used for our calculations of the single layer unit cell is simply the conventional unit cell with one of the [AgSePh]$_\infty$ layers removed. There is a 14 Å distance between the single layers of [AgSePh]$_\infty$ and [AgSeH]$_\infty$ layers due to the periodic boundary conditions used in our VASP calculations.

Calculation results

To explore the electronic properties of this system, we performed density functional theory (DFT) calculations with the VASP code using the hybrid functional of Heyd, Scuseria, and Ernzerhof (HSE), which includes approximate short-range exchange and correlation effects important for a balanced treatment of &localized sp valent and localized d and π states in [AgSePh]$_\infty$.

Figure 3:
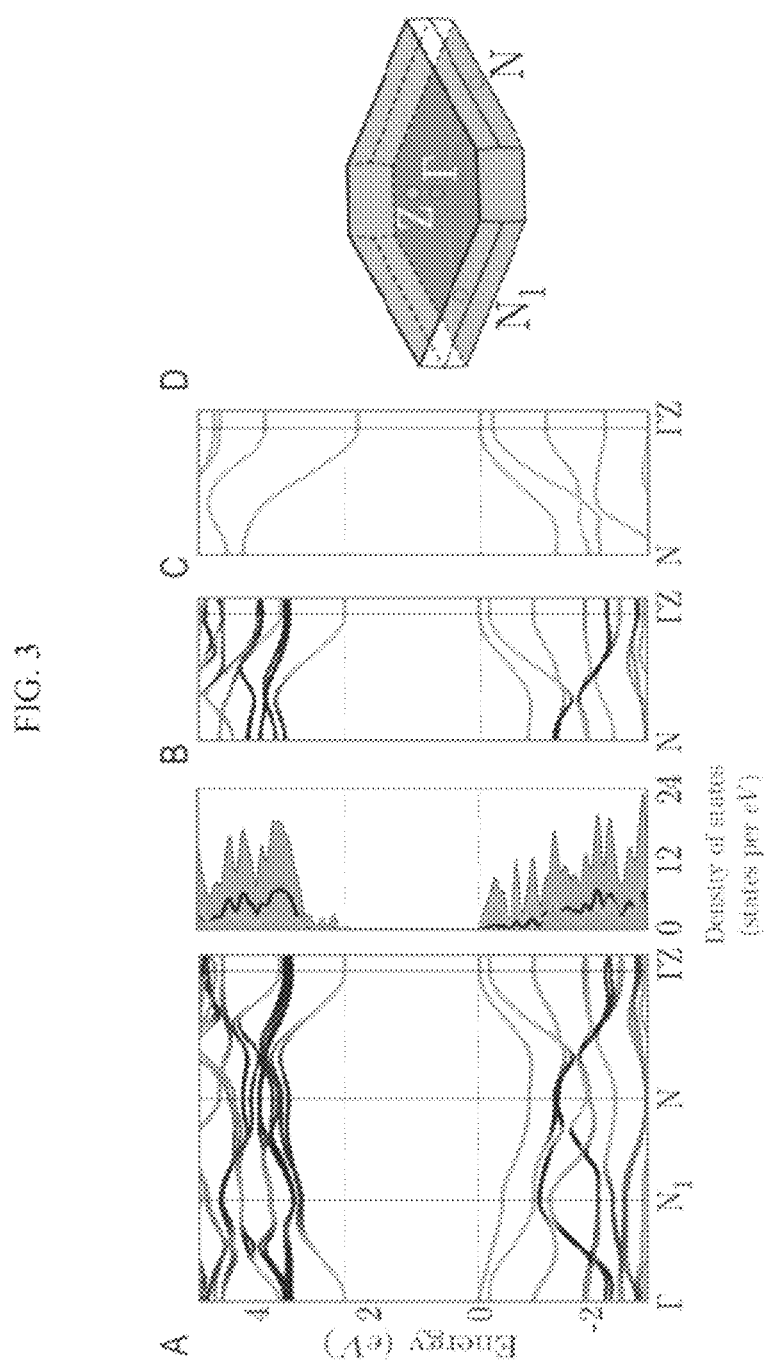
FIGS. 3a-d are illustrations of the band structures and density of states of bulk [AgSePh]$_\infty$, a single layer of [AgSePh]$_\infty$ and a single layer of [AgSePh]$_\infty$ with phenyl groups replaced with hydrogens. a) DFT-HSE band structure and density of states of bulk [AgSePh]$_\infty$. See FIG. 9 for details. Band color signifies the fractional contribution of states centered on inorganic (Ag and Se, orange) and organic (C and H, black) atoms in the crystal. The total density of states is shown in gray. b) DFT-HSE hand structure of a single layer of [AgSePh]$_\infty$, c) DFT-USE band structure of a single layer of [AgSePh]$_\infty$ with the phenyls replaced by hydrogen. The hydrogen positions have been relaxed with PBE; see FIG. 8. The near-band edge character remains relatively unchanged when the phenyls are replaced by hydrogen, suggesting that the degree of 2D quantum confinement is unchanged by 3D crystallization. d) The Brillouin zone for the primitive cell of [AgSePh]$_\infty$. The path in the Erillouin zone used for the band structure is identified by orange lines and k-point labels.

Using experimental lattice parameters and atomic positions, we performed calculations on the following periodic structures: (1) bulk [AgSePh]$_\infty$, (2) single-layer [AgSePh]$_\infty$, and (3) a single-layer [AgSePh]$_\infty$ with the phenyls replaced by hydrogen atoms. We used (1) and (2) to determine whether the layers of [AgSePb]$_\infty$ are electrically isolated and (3) to determine the impact of the ligand on the electronic structure. Our DFT band structures and density of states for these systems are shown in FIG. 3.

We found our computed band structures of bulk and single layer [AgSePh]$_\infty$ are indistinguishable, demonstrating that the layers of bulk [AgSePh]$_\infty$ are electrically isolated. Within DFT-HSE, bulk and single layer [AgSePh]$_\infty$ have a direct band gap at Γ of 2.4 eV, in good agreement with the measured photoluminescence, despite the tact that DFT is not expected, on formal grounds, to yield quantitative gaps. To obtain quantitative optical gaps and spectra, a more advanced treatment of exchange and correlation effects, including electron-hole interactions, is required in addition to our calculations, e.g., ab initio many-body perturbation theory (MBPT) within the OW approximation and the Bethe-Salpeter equation (BSE) approach.

The lowest-lying DFT-HSE conduction band of bulk [AgSeP]$_\infty$ is highly dispersive in plane, with electron effective masses of 1.13 me and 0.44 me, respectively, at Γ (Table 1). The effective masses at the direct gap, are similar for bulk and single layer [AgSePh]$_\infty$ and [AgSePh]$_\infty$ truncated with hydrogens. Only two principle directions are given for 2D single layer calculations. Bands exhibit significantly less dispersion perpendicular to the AgSe planes and along the stacking direction of [AgSePh]$_\infty$, with an electron effective mass of 18.7 me, reflecting weak interplanar coupling and suggesting significantly lower mobility along the [001] direction.

TABLE 1

Calculated effected masses at the direct gap of bulk, single and hydrogen-truncated [AgSePh]$_\infty$

| Structure | Principle Direction 1 | | Principle Direction 2 | | Principle Direction 3 | |
|---|---|---|---|---|---|---|
| Bulk | a | 1.130 | b | 0.441 | c* | 18.91 |
| Single Layer | a | 1.146 | b | 0.444 | — | — |
| Truncated | a | 0.466 | b | 0.298 | — | — |

Figure 4:
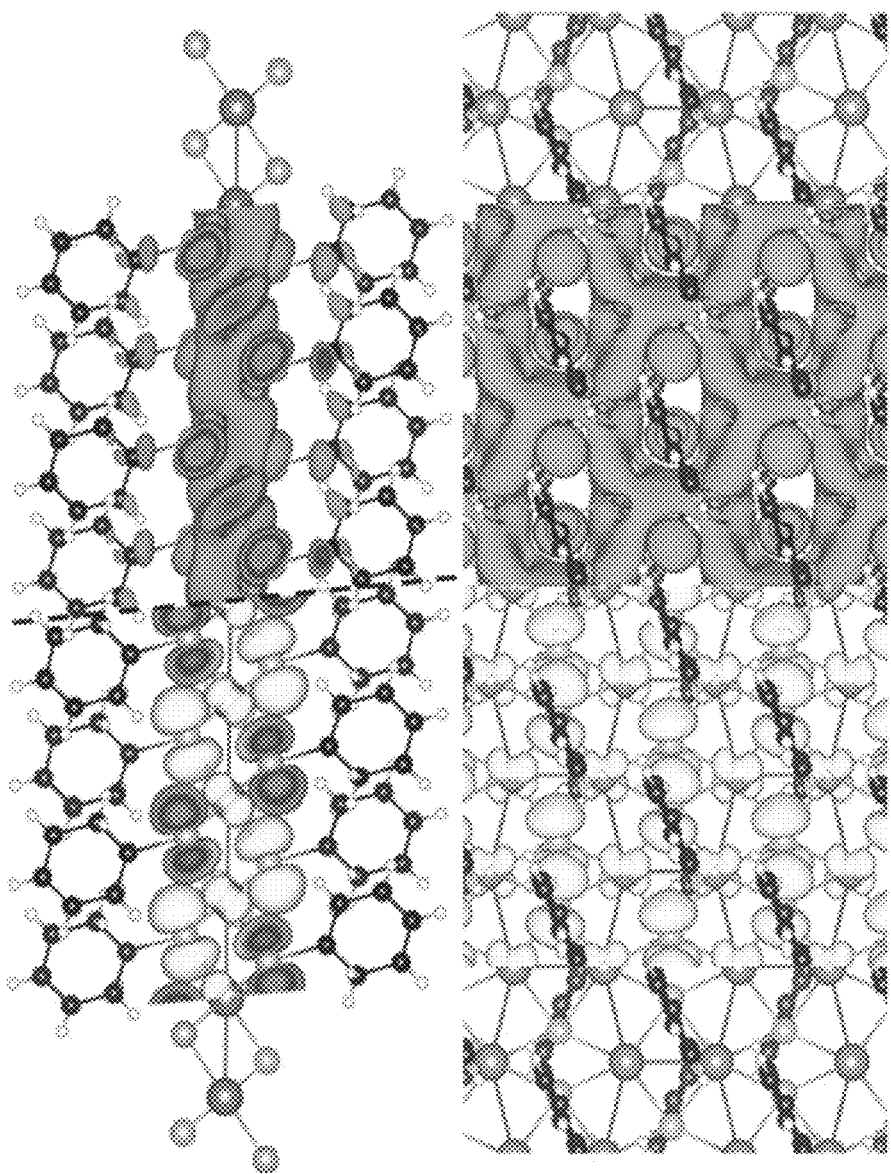
FIG. 4 is an illustration of the charge density associated with the bulk [AgSePh]$_\infty$ conduction band minimum and valence hand maximum states, containing depictions of side and top views of [AgSePh]$_\infty$ with overlain charge density maps. The DFT-HSE computed valence band maximum (VBM) and conduction band minimum (CBM) at Γ are accented in yellow and blue, respectively. The minimal but non-negligible participation of carbon in the CBM state suggests tailoring of electronic properties via synthetic modification of ligand.

The electronic structure of bulk and single layer [AgSePh]$_\infty$ near the valence and conduction band edges is dominated by contributions from silver selenide. FIG. 4 shows isosurfaces of the square of the wavefunction for the bulk [AgSePh]$_\infty$ conduction band minimum and valence hand maximum states at the Γ point. While the state at the valence hand maximum exhibits directional bonding associated with Ag 4d and Se 3p character, the conduction band minimum is more delocalized, featuring significant Ag 5s character. As seen in FIG. 4, the minimal contribution of p states from phenyl groups to band edge states—with valence hand maximum and conduction band minimum isosurface density visible only on the carbon atoms adjacent to the AgSe layer reflects the weak coupling between AgSe layers.

The calculated density of states shows a separation of bands having organic (phenyl) and inorganic (Ag and Se) character near the band gap. The phenyl π and π states are largely grouped at energies well below and above the Ag- and Se-rich valence and conduction band edges, respectively, consistent with the relatively large benzene gap (FIG. 3, Table 1) and minimal carbon character at the band edges (FIG. 4). Indeed, replacing the phenyl groups with hydrogen, we calculate that a hydrogen-truncated AgSe layer exhibits small changes in band gap and in-plane effective masses compared to the phenylated layer (FIG. 3). The relative alignment of the organic and inorganic states suggests an opportunity to tune the near-hand edge character of each component via ligand choice. A ligand with a smaller band gap, such as pentacene, could contribute states hybridizing with those of silver selenide at the band edge. Thus, it may he possible to tune electronic properties of this system, as well as the coupling between layers, by ligand design. The use of ligands has been successfully used to tune the optoelectronic properties of quantum dots; we can apply the same principles to metal-organic crystalline systems described here.

Previous experiments and ab initio MBPT calculations on TMDs have established large exciton binding energies, novel screening effects, and trion formation. Given the similarity of its atomic structure to that of 2D TMDs, and the added presence of the phenyl ligands, such excited state phenomena are also likely to emerge from this silver selenide system.

To assess DFT's ability to reproduce the experimental structure, we relaxed the experimentally reported crystal structure, choosing the lower energy of the two possible phenyl configurations reported in space group 15, with LDA, PBE, and df2 functionals (with PBE pseudopotentials). A summary of the relaxation results, including percentage change in lattice parameters, variables describing the Ag lattice, and the dihedral angle between above and below plane phenyls, is given in Table 2. The structures were relaxed until the stress on the unit cell was less than 0.5 kBar. Tables 2-6, below, provide the crystallographic unit cell lattice parameters and Wyckoff positions for the experimental crystal structure and density functional theory relaxations of the experimental crystal structure with 3 different functions (LDA, PBE, and df2).

TABLE 2

Relaxation Table

| Functional | (a/aexp− 1) | (b/bexp − 1) | (c/cexp − 1) | (β/βexp − 1) | θ1 | θ2 = θ3 | l1 = l2 | l3 | Dihedral Angle |
|---|---|---|---|---|---|---|---|---|---|
| Experiment | — | — | — | — | 152 | 104 | 3.029 | 2.911 | 52 |
| LDA | −1.17% | −1.97% | −2.62% | −0.65% | 152 | 104 | 2.993 | 2.849 | 29 |
| PBE | 6.18% | 7.86% | 0.43% | −0.65% | 170 | 95 | 3.132 | 3.656 | 28 |
| df2 | 2.74% | 10.54% | 1.11% | −0.92% | 154 | 103 | 3.099 | 3.332 | 38 |

TABLE 3

Wyckoff Position Table: Experimental Structure from Cuthbert et al.
Cuthbert
Spacegroup: 15 (C2/c)

| a | b | c |
|---|---|---|
| 5.876 | 7.299 | 29.124 |

| α | β | γ |
|---|---|---|
| 90 | 95.79 | 90 |

| Label | x | y | z | Wyckoff letter |
|---|---|---|---|---|
| Ag1 | 0.5 | 0.381 | 0.25 | e |
| Ag2 | 0.5 | 0.982 | 0.25 | e |
| C1 | 0.671 | 0.186 | 0.141 | f |
| C2 | 0.453 | 0.258 | 0.127 | f |
| C3 | 0.369 | 0.267 | 0.081 | f |
| C4 | 0.807 | 0.11 | 0.108 | f |
| C5 | 0.496 | 0.191 | 0.049 | f |
| C6 | 0.716 | 0.12 | 0.06 | f |
| H1 | 0.439 | 0.199 | 0.018 | f |
| H2 | 0.447 | 0.555 | 0.116 | f |
| H3 | 0.802 | 0.08 | 0.037 | f |
| H4 | 0.729 | 0.823 | 0.072 | f |
| H5 | 0.363 | 0.3 | 0.15 | f |
| Se1 | 0.792 | 0.182 | 0.205 | f |

TABLE 4

Wyckoff Position Table: DFT relaxation with LDA functional
LDA
Spacegroup: 15 (C2/c)

| a | b | c |
|---|---|---|
| 5.807 | 7.155 | 28.361 |

| α | β | γ |
|---|---|---|
| 90 | 95.163 | 90 |

| Label | x | y | z | Wyckoff letter |
|---|---|---|---|---|
| Ag1 | 0.5 | 0.363 | 0.75 | e |
| Ag2 | 0 | 0.262 | 0.75 | e |
| C1 | 0.277 | 0.061 | 0.86 | f |
| C2 | 0.058 | 0.02 | 0.873 | f |
| C3 | 0.022 | 0.021 | 0.921 | f |
| C4 | 0.457 | 0.103 | 0.893 | f |
| C5 | 0.201 | 0.063 | 0.955 | f |
| C6 | 0.419 | 0.104 | 0.941 | f |
| H1 | 0.171 | 0.066 | 0.992 | f |
| H2 | 0.627 | 0.141 | 0.882 | f |
| H3 | 0.561 | 0.141 | 0.968 | f |
| H4 | 0.351 | 0.483 | 0.931 | f |
| H5 | 0.418 | 0.483 | 0.846 | f |
| Se1 | 0.338 | 0.062 | 0.794 | f |

TABLE 5

Wyckoff Position Table: DFT relaxation with PBE functional
PBE
Spacegroup: 15 (C2/c)

| a | b | c |
|---|---|---|
| 6.239 | 7.873 | 29.248 |

| α | β | γ |
|---|---|---|
| 90 | 95.166 | 90 |

| Label | x | y | z | Wyckoff letter |
|---|---|---|---|---|
| Ag1 | 0.5 | 0.328 | 0.25 | e |
| Ag2 | 0 | 0.292 | 0.25 | e |
| C1 | 0.259 | 0.061 | 0.356 | f |
| C2 | 0.059 | 0.025 | 0.372 | f |
| C3 | 0.036 | 0.028 | 0.419 | f |
| C4 | 0.436 | 0.099 | 0.387 | f |
| C5 | 0.212 | 0.066 | 0.45 | f |
| C6 | 0.411 | 0.102 | 0.434 | f |
| H1 | 0.193 | 0.07 | 0.487 | f |
| H2 | 0.591 | 0.129 | 0.374 | f |
| H3 | 0.549 | 0.134 | 0.458 | f |
| H4 | 0.379 | 0.499 | 0.431 | f |
| H5 | 0.422 | 0.494 | 0.347 | f |
| Se1 | 0.29 | 0.06 | 0.29 | f |

TABLE 6

Wyckoff Position Table: DFT relaxation with df2 functional
PBE + VdW
Spacegroup: 15 (C2/c)

| a | b | c |
|---|---|---|
| 6.037 | 8.068 | 29.446 |

| α | β | γ |
|---|---|---|
| 90 | 94.904 | 90 |

| Label | x | y | z | Wyckoff letter |
|---|---|---|---|---|
| Ag1 | 0.5 | 0.393 | 0.25 | e |
| Ag2 | 0.5 | 0.98 | 0.25 | e |
| C1 | 0.665 | 0.188 | 0.139 | f |
| C2 | 0.445 | 0.237 | 0.127 | f |
| C3 | 0.365 | 0.237 | 0.081 | f |
| C4 | 0.803 | 0.14 | 0.105 | f |
| C5 | 0.502 | 0.188 | 0.047 | f |
| C6 | 0.721 | 0.14 | 0.059 | f |
| H1 | 0.439 | 0.188 | 0.011 | f |
| H2 | 0.472 | 0.6 | 0.115 | f |
| H3 | 0.829 | 0.099 | 0.034 | f |
| H4 | 0.696 | 0.778 | 0.071 | f |
| H5 | 0.339 | 0.278 | 0.152 | f |
| Se1 | 0.787 | 0.186 | 0.204 | f |

LDA gave the best agreement with experiment with isotropic changes in lattice parameters of less than 3%. The df2 with PBE pseudopotentials give anisotropic expansion of the b lattice parameters. PBE gave the worst agreement with experiment with 7% increases in a and b lattice parameters lying in the AgSe plane. Df2 gives the best agreement with the dihedral angle between above and below layer phenyl ligands, However, the distortion of the Ag lattice shows poor description of the covalently bonded AgSe layer. The relaxations were insensitive to an increase in the basis energy cutoff and adding a U=5 eV to Ag atoms.

The dihedral angle for the phenyl groups was determined by fitting Miller planes to a phenyl group from each orientation in VESTA and calculating the angle between the planes' normal vector.

The band structure of the dig relaxed structure shows a greater separation between hands of inorganic and organic character, with the bands of organic character moving away from the Fermi level. Otherwise, the bands remain largely unchanged.

The effective masses of [AgSePh]$_\infty$ at the direct band gap were calculated using the EMC The hand structures and densities of state were plotted using a modified version pymatgen.

Example 1. Miscible Gram-Scale, Solution Phase Synthesis of [AgSePh]$_\infty$.

An oven dried round bottom flask equipped with a stir bar was charged with silver nitrate (1.4 g, 0.008 mol) and triphenylphosphine (4.4 g, 0.017 mol) in 250 mL of dry tetrahydrofumn. The solution was stirred for 16 h under nitrogen at ambient temperature giving a cloudy, white suspension. Diphenyl diselenide (1.3 g, 0.004 imp in 80 mL of dry tetrahydrofuran was then added slowly to the flask at −50° C. The reaction was stirred while warming slowly to room temperature in which a deep yellow solution resulted. The solution is layered with 75 mL of diethyl ether and stirred rapidly until solution is clear and colorless and bright yellow crystals have precipitated. The solvent is decanted and the solid was purified by the addition of fresh isopropyl alcohol followed by sonication and centrifugation to separate the crystalline pellet and supernatant. The crystals are then dried under vacuum giving a canary yellow tine powder (2.3 g isolated).

Example 2. Immiscible Solution Interface Synthesis of [AgSePh]$_\infty$.

In a glass scintillation vial, 5 mL of 3 mM diphenyl diselenide in toluene solution was carefully layered over 5 mL of a 3 mM aq. silver nitrate solution and allowed to crystallize at room temperature for 3 days. Crystals were recovered by passing a substrate, glass or silicon, through the liquid interface into the aqueous phase, and then gently pulling the substrate at a 45 degree angle back into the organic phase. The crystals preferentially adhered to the solid substrate. Poor adhesion is noted when hydrophobic substrates are used; pristine silicon wafers gave poor results, as did gold, which becomes rapidly functionalized with benzeneselenolate monolayers on exposure to the organic layer. Gentle drying by forced air is generally acceptable for most analyses, although an absorbent laboratory wipe can he used to wick residual liquids from the surface. Alternatively, suspensions of the crystals can be isolated by removing the aqueous layer from their reaction vessel using a glass pipette, and then decanting the toluene layer leaving behind the crystals. The product is then dispersed in isopropanol and sonicated briefly to remove any residual crystals off the sides of the glassware, and then palletizes readily from isopropanol under centrifugation. The crystals are stored in the dark under vacuum (<1 mg isolated per crystallization vial).

Example 3. Standard Chemical Vapor Deposition Procedure ("Tarnish").

A specified amount of ligand (typically 20-50 mg) was placed into a small glass vial. The vial was placed into a glass jar (FIG. 12). The silver-coated substrates were placed on the floor of the glass jar. The jar was tightly capped and placed into a warmed oven (80° C.). After the specified amount of time (overnight, a few days, or a week), the jars were taken from the oven, opened, and the samples removed.

Example 4. Tarnish Study.

Figure 13:
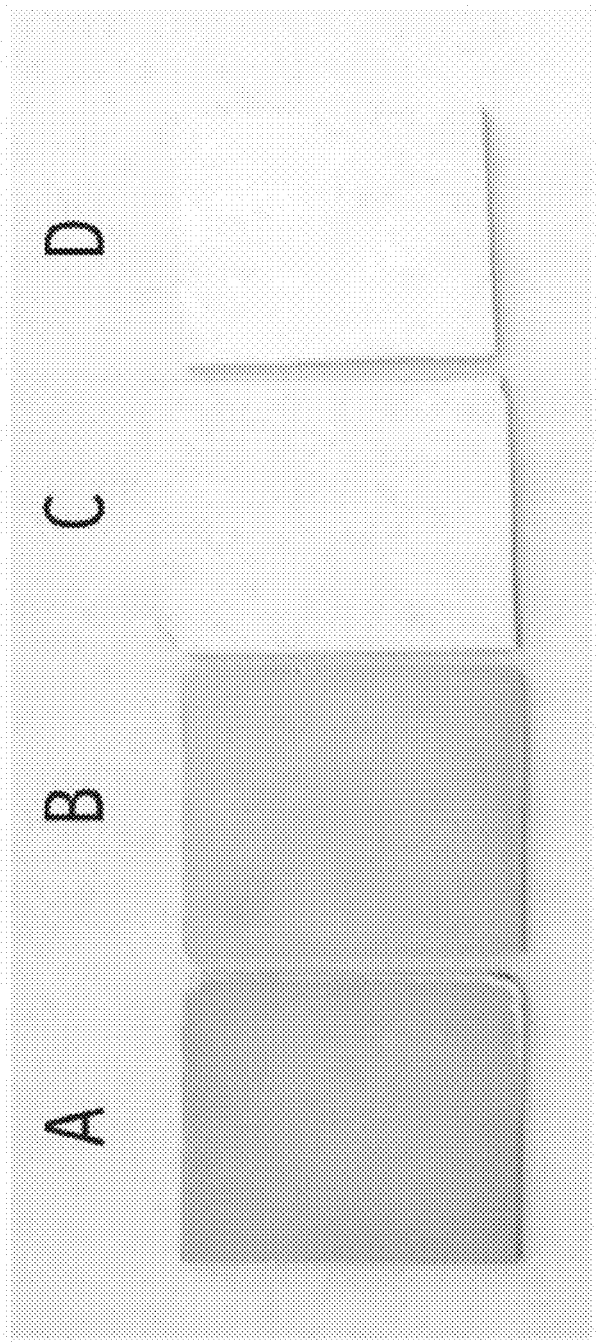

Since the presence of water is necessary for tarnishing to occur, regardless of what the exact tarnishing mechanism might be, we tested the effect of water content on our mithrene wafer synthesis. A control wafer was run in ambient air, another water was run in a vessel containing calcium chloride desiccant, and a third wafer was run in a vessel containing 0.2 mL of water. The appearances of the three product wafers appeared markedly different (FIG. 13). The wafer grown in humid conditions appeared more tarnished than the wafer grown in ambient conditions; the one containing desiccant appeared silver (nearly like the starting wafer) and almost unreacted. FIG. 14 shows the diffuse reflectance of a silver mirror and the sample grown in a dry atmosphere. The spectra are nearly identical, showing that very few if any mithrene layers formed on the dry sample's surface. This clear reliance on the relative humidity of the synthesis atmosphere strengthens the relationship between the mithrene wafer synthesis and tarnishing.

Figure 15:
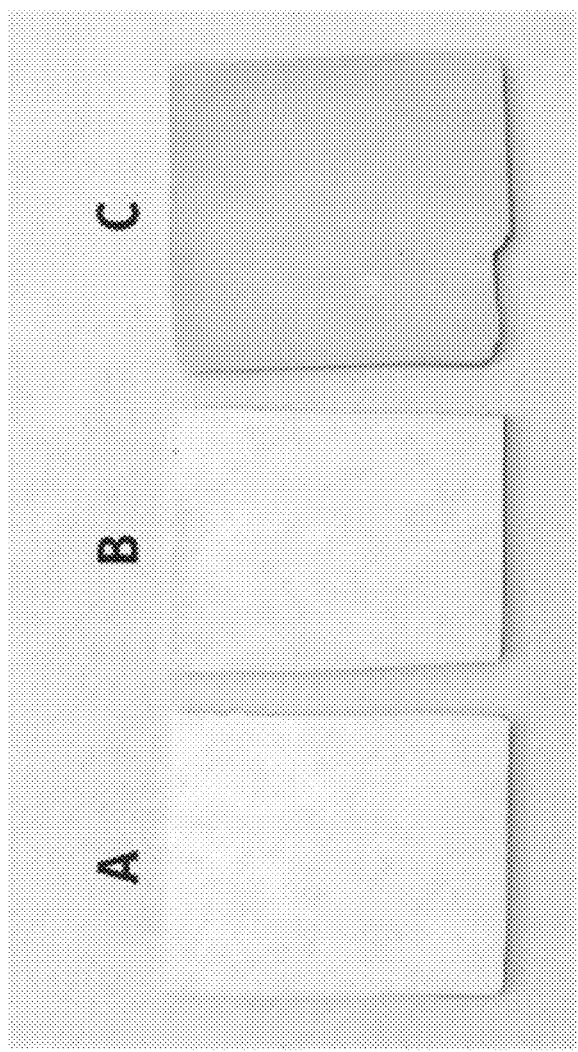

To examine the role of oxygen in the reaction, a reaction was carried out in a nitrogen glovebox. As seen in FIG. 15, the sample tarnished considerably less than the control sample, but if the reaction were mediated by water and oxygen, there should have been absolutely no reaction. The level of oxygen in the glovebox ranged from approximately 11-13 ppm, so it is possible that the presence of trace oxygen facilitated the reaction. However, the box also showed that there was less than 0.1 ppm of water in the glovebox, which means that the experiment should have tarnished even less than the "dry" sample in the humidity study. Regardless of whether oxygen is a key component of the reaction mechanism, these results call into question both the integrity of the glovebox's water and oxygen monitors as well as the role of calcium chloride in preventing the tarnishing reaction.

Example 5. Time Course Study.

A time study was run to investigate mithrene's growth mechanism. Samples were placed in an 80° C. oven at 24-hour intervals to create 1-, 2-, 3-, 6-, and 7-day samples, then were analyzed by cross-sectional SEM. The SEM revealed that the amount of silver consumed increased over time, showing that the diphenyldiselenide seems to penetrate the material formed on top and reacts with the covered silver surface (FIG. 16).

The cross-sectional SEM showed that the edges of the mithrene films had lifted off the silicon surface over time, so another time study was run using silicon waters that were coated first with 5 nm of a titanium adhesion layer, then 200 nm of silver. The time study was run with six samples at 1-, 2-, 3-, 4-, 7-, and 8-day time points.

SEM studies of samples from the first and eighth days showed the formation of mithrene on the surface. In the image from the first day (FIG. 17b), small, not-well-defined squares of mithrene lie on top of the bumpy silver surface. In the image from the eighth day (FIG. 17c), numerous squares of mithrene lie on top of each other, covering the entire silver surface.

Example 6. Thickness Study.

Figure 18:
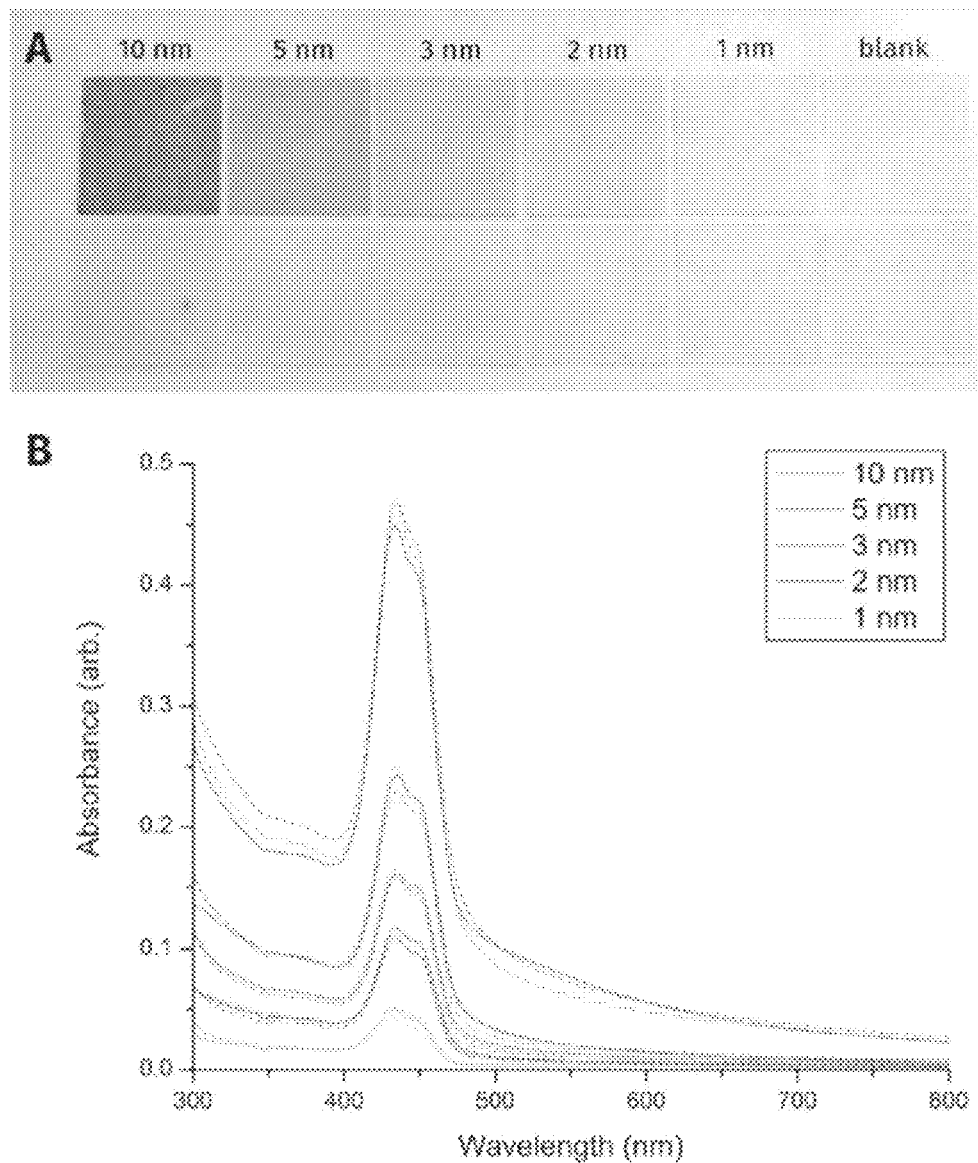

To study the optical properties of the mithrene films in greater detail, a series of fully-converted niithrene films were grown on transparent glass coverslips. This series used different initial thicknesses of silver to create different thicknesses of niithrene. UV-vis absorption spectra of the series of films showed a linear relationship between film thickness and absorbance (FIG. 18). The thickness of the mithrene films was calculated in order to make a Beer's Law plot. The mithrene thickness was calculated using the following formula (Formula II):

$$[((\text{area of film} \times \text{thickness of film} \times \text{density of silver}) \\ \text{atomic mass of silver}) \times \text{molar mass of AgSePh}] / \\ \text{area of film} \times \text{density of AgSePh}$$

Using this method, the calculated height of a mithrene layer corresponded to about 9 nm mithrene per 1 nm silver, or about 7 layers mithrene per 1 nm silver (using a 1.4 nm mithrene layer height). The number of layers ranged from 65 layers for the 10 nm sample to 7 layers for the 1 nm sample. Using these calculated layers of mithrene and the absorption of the films at the 434 nm maximum, a Beer's Law plot was generated (FIG. 19), which formed a very linear fit that gave an absorption coefficient of 0.00689.

Regardless of the accuracy of the silver deposited and the amount mithrene grown, this study demonstrates that the light attenuation varies linearly with the number of mithrene layers.

Example 7. Alloy Study.

One can extend the chalcogenide chemistry from selenium to tellurium, selenium's fifth-row analogue, and create silver benzenetellurolate (tethrene). Films of 10 nm silver deposited on quartz substrates were converted to films of mithrene, tethrene, and mithralloy (synthesized with a mixture of diphenyl diselenide and diphenyl ditelluride). UV-vis absorption spectra showed that mithrene gave one peak with a shoulder around 440 nm, tethrene gave a doublet with peaks around 410 and 470 nm, and mithralloy gave two peaks around 440 and 460, right between the peaks of its parent materials mithrene and tethrene.

A further study used mithrene-tethrene alloy films which Were grown using diphenyl diselenide and diphenyl ditelluride ligand in 1:0.33, 1:1, and 1:3 molar ratios. The colors of the films (FIG. 20) ranged from yellow (mithme) to yellow-orange (alloys) to orange (tethrene). UV-vis (FIG. 21) and photoluminescence data (FIG. 22) showed that the materials increased in tethrene-like behavior as the amount of diphenyl ditelluride ligand increased.

The photoluminescence spectra (FIG. 22) show the stark differences between the mithrene sample and the samples that contained diphenyl ditelluride. The mithrene sample gave a single, sharp peak around 470 nm, whereas all of the telluride-containing samples gave broad peaks centered around 600 nm. This difference in emission/absorption wavelength indicates that while mithrene seems to be a direct-gap semiconductor, tethrene may be an indirect-gap semiconductor. The broad peaks increased in intensity as the ratio of diphenyl ditelluride brand increased. However, the sudden shift in the behavior of the samples once telluride ligands were introduced to the system prompted a further study using very small (1:0.05, 1:0.10, and 1:0.20) molar ratios of diphenyl diselenide to diphenyl ditelluride.

The alloy study using smaller amounts of tellurium ligand further showed the progression from mithrene-like behavior to tethrene-like behavior the doublet excitonic absorption peak continued to spread away from each other as tellurium content rose (FIG. 23). The samples also showed that the tethrene-like behavior still dominated even at selenide:telluride ratios of 1:0.05.

One sample (1:0.10) seemed to be an outlier; even though the recorded masses of the ligands used to synthesize the sample were very close to the desired ratio (1:0.099), the sample was visibly more orange than its neighbors (FIG. 24) and its absorbance showed peaks more in accordance with a sample that had a 1:1 selenide:telluride ratio.

Example 8. Transchalcogenation.

We attempted another variation on the alloying theme: transchalcogenation, or turning a mithrene film into a tethrene film and vice-versa (FIG. 25). 10 nm silver on glass films and 200 nm silver 5 nm titanium on silicon wafers were heated for two days in either a diphenyl diselenide or a diphenyl ditelluride atmosphere, then the vials of ligand were switched and the films were heated for another two days in the opposite atmosphere.

As seen in FIG. 25, the silicon transchalcogenation samples appear different from their control samples the— mithrene>tethrene sample is more orange than the mithrene control, and the tethrene: mithrene sample is more yellow than the tethrene control. However, the glass transchalcogenation films look much like the control samples, as seen in the absorbance spectra in FIG. 26.

Figure 27:
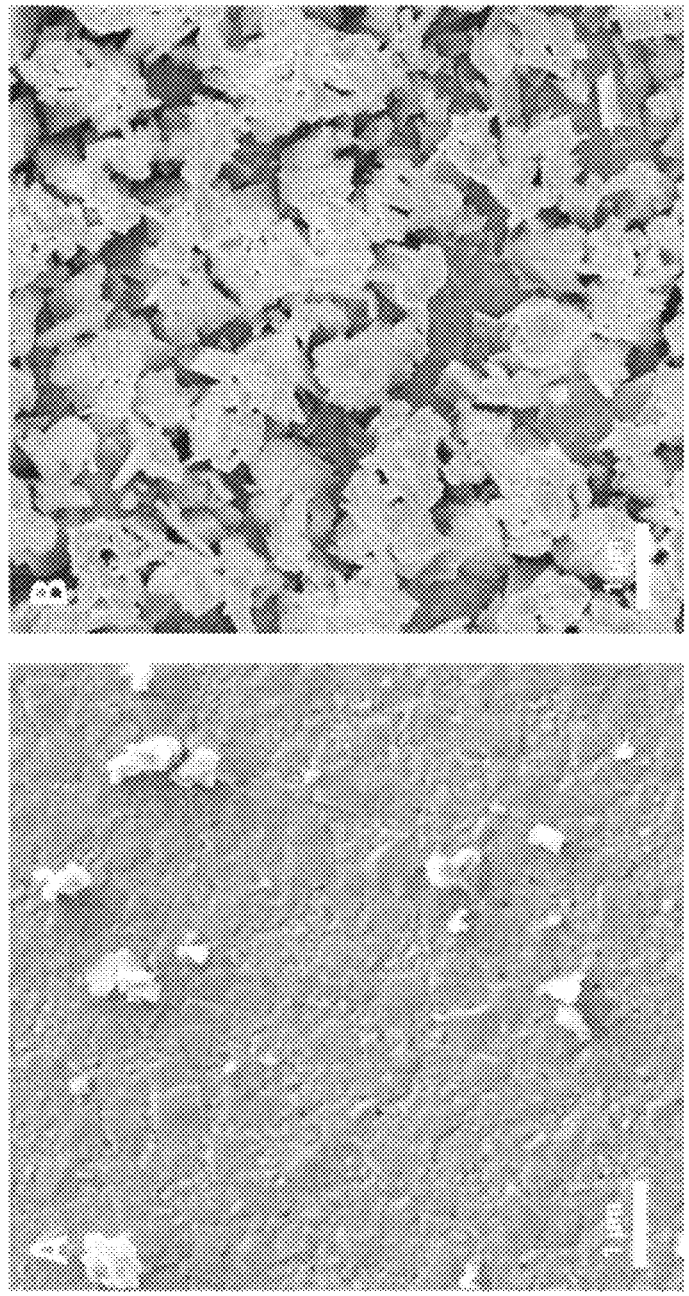

The glass transchalcogenation samples may appear to be much like their control samples because the 10 nm layer of silver on the glass samples was consumed during the phase of synthesis with the initial ligand and had no silver left to react with the secondary ligand, whereas the silicon samples had a 200 nm layer of silver and thus unconsumed silver was available beneath the initial layer and could react with the second chalcogen ligand. This theory is supported by SEM images of the samples (FIG. 27)

The lighter-colored clusters in the SEM images are presumably secondary chaleogen growths. As seen in FIG. 27a, the mithrene>tethrene sample has very few tethrene growths, presumably due to the faster reaction time of diphenyl diselenide that contributed to a more-complete coverage of the initial mithrene layer. FIG. 27b shows many light-colored mithrene growths, possibly due to the patchier initial tethrene layer, which allowed many mithrene towers to grow from the silver that was exposed through the cracks. The relative rate of reaction of the two materials also explains the size of the clusters: since tethrene is slower-growing, its clusters are much smaller in size than the mithrene clusters, which are several layers tall.

The absorption spectra for the films corroborate this theory as well; the mithrene and mithrene>tethrene films are similar in shape but differ slightly in intensity, while the tethrene>mithrerie film has peaks that are closer together than the peaks in the tethrene control spectrum and that look much like the peaks in the alloy samples. This greater exemplification of alloy behavior in the tethrene>mithrene film as compared to the mithrerie>tethrene film may be attributed to the larger molecular weight of the telluride ligand as compared to the selenide ligand and the telluride ligand's accordingly slower reaction kinetics.

However, all of these explanations rely on the assumption that tethrene growth is in fact slower than mithrene growth. This effect has only been observed anecdotally and a tethrene time study is needed to corroborate these observations.

However, these calculations are still an estimate of the actual absorption coefficient because of the assumptions that the surfaces of the wafers were uniformly coated in silver and, more importantly, that the silver thicknesses indicated by the thermal evaporator control were indeed the absolute thicknesses. Estimates of the absolute accuracy of the evaporator's quartz crystal microbalance suggested that the absolute thicknesses may have been only about 60% of the indicated thicknesses, resulting in fewer layers (ranging from 39 layers for the 10 nm sample to 4 for the 1 nm sample) and a higher extinction coefficient (0.01149).

Reference throughout this specification to "one embodiment," "certain embodiments," "one or more embodiments" or "an embodiment" means that a particular feature, structure, material, or characteristic described in connection with the embodiment is included in at least one embodiment of the present disclosure. Thus, the appearances of the phrases such as "in one or more embodiments," "in certain embodiments," "in some embodiments," "in one embodiment," or "in an embodiment" in various places throughout this specification are not necessarily referring to the same embodiment of the present disclosure. Furthermore, the particular features, structures, materials, or characteristics may be combined in any suitable manner in one or more embodiments. All of the various embodiments, aspects, and options disclosed herein can be combined in all variations. The scope of the compositions, formulations, methods, and processes described herein include all actual or potential combinations of embodiments, aspects, options, examples, and preferences herein.

Although the embodiments disclosed herein have been described with reference to particular embodiments it is to be understood that these embodiments are merely illustrative of the principles and applications of the present disclosure. It will be apparent to those skilled in the art that various modifications and variations can be made to the methods and apparatus of the present disclosure without departing from the spirit and scope of the disclosure. Thus, it is intended that the present disclosure include modifications and variations that are within the scope of the appended claims and their equivalents, and the above-described embodiments are presented for purposes of illustration and not of limitation. All patents and publications cited herein are incorporated by reference herein for the specific teachings thereof as noted, unless other statements of incorporation are specifically provided.

What is claimed is:

1. A method of preparing a crystalline metal chalcogenide of Formula 1: $[M-Z-Ar]_\infty$, the method comprising:
   providing a first solution comprising a metal ion, $M^+$, in a first solvent, the metal ion obtained by dissolving a metal component, $M_pX_q$, in the first solvent;
   providing a second solution comprising a diaryl dichalcogenide, Ar-Z-Z-Ar, in a second solvent; and
   contacting the first solution with the second so ion to provide the metal chalcogenide a crystalline, bulk nanomaterial; wherein:
   M is selected from the group consisting of silver (Ag), lead (Pb), mercury (Hg), gold (Au), copper (Cu) zinc (Zn), tin (Sn), cobalt (Co), thallium (Tl), (Ga), indium (In) and cadmium (Cd);
   p is 1 or 2;
   X is an oxide or salt selected from the group consisting of O, $NO_3$, $SO_4$, Cl, Br, $CH_3CO_2$, $CF_3SO_3$, $PF_6$, $BF_4$, and $ClO_4$;
   q is 1, 2, or 3;
   Z is sulfur, selenium, tellurium, or combinations thereof; and
   Ar is phenyl or naphthyl.

2. The method of claim 1, wherein M is Ag.

3. The method of claim 1, wherein the metal component is $AgNO_3$.

4. The method of claim 1, wherein the first solvent and second solvent are immiscible.

5. The method if claim 4, wherein the first solvent is water and the second solvent is an aromatic hydrocarbon.

6. The method of claim 5, wherein the second solvent is toluene.

7. The method of claim 4, wherein the contacting occurs at the interface of the first and second solvents.

8. The method of claim 7, wherein the contacting occurs over a period from about to about 1 to about 3 days.

9. The method of claim 7, wherein the contacting occurs at a temperature from about 15° C. to about 100° C.

10. The method of claim 4, further comprising recovering the crystalline metal chalcogenide by adhering the crystalline material to a substrate.

11. The method of claim 10, wherein the adhering is performed by passing the substrate through the liquid interface into the first solution, and withdrawing the substrate through the second solution at an angle of about 45 degrees.

12. The method of claim 4, further comprising recovering the crystalline metal chalcogenide by:
   removing the first solution while retaining the crystalline material and the second solution;
   removing the second solution while retaining the crystalline material; and
   collecting the crystalline material.

13. The method of claim 10, wherein the substrate is glass or silicon.

14. The method of claim 1, wherein the concentration of metal ion $M^+$ in the first solution is about 0.1 mM to about 100 mM.

15. The method of claim 1, wherein the concentration of diaryl dichalcogenide in the second solution is about 0.1 mM to about 100 mM.

16. The method of claim 1, wherein the first solvent and the second solvent are miscible.

17. The method of claim 16, wherein the contacting further comprises:
   a) adding a stabilizing ligand to the first solution with stirring under an inert atmosphere;
   b) cooling the resulting solution to a temperature of about −80° C. to about 0° C.;
   c) adding the second solution to the cold first solution with stirring;
   d) warming the resulting solution from c) to a temperature of about 20° C. to about 30° C. while stirring;
   e) diluting the solution of d) with a dilution solvent while rapidly stirring until the mixture is clear and colorless; and
   f) collecting the crystalline product by decanting or filtering.

18. The method of claim 16, wherein the first solvent and second solvent are independently selected from the group consisting of tetrahydrofuran acetonitrile, dimethylsulfoxide, pyridine, chloroform, dichloromethane, benzene, toluene, and methanol.

19. The method of claim 16, wherein the first solvent and second solvent are the same.

20. The method of claim 19, wherein the first solvent and second solvent are THF.

21. The method of claim 17, wherein the stabilizing ligand is a phosphine.

22. The method of claim 17, wherein the stabilizing ligand is triphenylphosphine.

23. The method of claim 17, wherein the dilution solvent is diethyl ether or an aliphatic hydrocarbon.

24. A vapor phase deposition method of preparing a substrate coated with a film comprising a metal chalcogenide of Formula I: $[M-Z-R]_\infty$, the method comprising:
   providing a substrate comprising a coating of a metal, M, or an oxide thereof; and
   exposing the substrate coated with metal to a vapor phase comprising a first dialkyl or diaryl dichalcogenide, $R_2Z_2$, for a time sufficient to provide a film of a first $[M-Z-R]_\infty$ on the substrate; wherein:
   the metal or oxide thereof is selected from the group consisting of silver, titanium, zinc, lead, copper, indium, gallium and cadmium;
   Z is sulfur, selenium, tellurium, or combinations thereof; and
   R is phenyl, naphthyl, biphenyl, methyl, ethyl, propyl, butyl or pentyl.

25. The method of claim 24, wherein M is silver or silver oxide, Z is selenium, and R is phenyl.

26. The method of claim 24, wherein the time is from about 12 hours to about 14 days.

27. The method of claim 24, wherein the exposing is conducted at a temperature from about 15° C. to about 100° C.

28. The method of claim 24, wherein the substrate is glass, quartz, silicon or plastic.

29. The method of claim 24, wherein the coating of metal on the substrate is about 1 nm to about 100 nm in thickness.

30. The method of claim 24, wherein the coating of metal on the substrate comprising a first and second layer, the first layer comprising titanium and the second layer comprising silver or silver oxide.

31. The method of claim 24, wherein the vapor phase further comprises water.

32. The method of claim 31, wherein the vapor phase is saturated with water.

33. The method of claim 31, wherein the vapor phase further comprises oxygen.

34. The method of claim 24, the method further comprising:
   exposing the substrate coated with a film of the first $[M-Z-R]_\infty$ to a second dialkyl diaryl dichalcogenide, $R_2Z_2$, in the vapor phase for a time sufficient to provide a film of the second $[M-Z-R]_\infty$ on the substrate; wherein:
   the first and second dialkyl or diaryl dichalcogenide are different, and the first and second $[M-Z-R]_\infty$ are different.

35. The method of claim 34, wherein the film of the first $[M-Z-R]_\infty$ is $[Ag-Se-Ph]_\infty$ and the film of the second $[M-Z-R]_\infty$ is $[Ag-Te-Ph]_\infty$.

\* \* \* \* \*